US008652780B2

(12) United States Patent
Ehrich et al.

(10) Patent No.: US 8,652,780 B2
(45) Date of Patent: Feb. 18, 2014

(54) RESTRICTION ENDONUCLEASE ENHANCED POLYMORPHIC SEQUENCE DETECTION

(75) Inventors: Mathias Ehrich, San Diego, CA (US); Dirk Johannes Van den Boom, La Jolla, CA (US)

(73) Assignee: Sequenom, Inc., San Diego, CA (US)

( * ) Notice: Subject to any disclaimer, the term of this patent is extended or adjusted under 35 U.S.C. 154(b) by 253 days.

(21) Appl. No.: 12/532,824

(22) PCT Filed: Mar. 26, 2008

(86) PCT No.: PCT/US2008/058317
§ 371 (c)(1),
(2), (4) Date: Mar. 15, 2010

(87) PCT Pub. No.: WO2008/118988
PCT Pub. Date: Oct. 2, 2008

(65) Prior Publication Data
US 2012/0115737 A1    May 10, 2012

Related U.S. Application Data

(60) Provisional application No. 60/908,167, filed on Mar. 26, 2007.

(51) Int. Cl.
*C12Q 1/68* (2006.01)

(52) U.S. Cl.
USPC ........................................................ 435/6.12

(58) Field of Classification Search
None
See application file for complete search history.

(56) References Cited

U.S. PATENT DOCUMENTS

| | | |
|---|---|---|
| 4,656,127 A | 4/1987 | Mundy |
| 4,683,195 A | 7/1987 | Mullis et al. |
| 4,683,202 A | 7/1987 | Mullis et al. |
| 4,851,331 A | 7/1989 | Vary et al. |
| 4,965,188 A | 10/1990 | Mullis et al. |
| 5,210,015 A | 5/1993 | Gelfand et al. |
| 5,387,505 A | 2/1995 | Wu |
| 5,484,701 A | 1/1996 | Cocuzza et al. |
| 5,487,972 A | 1/1996 | Gelfand et al. |
| 5,492,806 A | 2/1996 | Drmanac et al. |
| 5,525,464 A | 6/1996 | Drmanac et al. |
| 5,547,835 A | 8/1996 | Koster |
| 5,589,330 A | 12/1996 | Shuber |
| 5,605,798 A | 2/1997 | Koster |
| 5,641,658 A | 6/1997 | Adams et al. |
| 5,656,493 A | 8/1997 | Mullis et al. |
| 5,679,524 A | 10/1997 | Nikiforov et al. |
| 5,691,141 A | 11/1997 | Koster |
| 5,695,940 A | 12/1997 | Drmanac et al. |
| 5,786,183 A | 7/1998 | Ryder et al. |
| 5,834,189 A | 11/1998 | Stevens et al. |
| 5,849,483 A | 12/1998 | Shuber |
| 5,849,542 A | 12/1998 | Reeve et al. |
| 5,851,770 A | 12/1998 | Babon et al. |
| 5,869,242 A | 2/1999 | Kamb |
| 5,876,934 A | 3/1999 | Duthie et al. |
| 5,891,625 A | 4/1999 | Buchardt et al. |
| 5,908,755 A | 6/1999 | Kumar et al. |
| 5,912,118 A | 6/1999 | Ansorge et al. |
| 5,928,906 A | 7/1999 | Koster et al. |
| 5,952,174 A | 9/1999 | Nikiforov et al. |
| 5,958,692 A | 9/1999 | Cotton et al. |
| 5,976,802 A | 11/1999 | Ansorge et al. |
| 5,981,186 A | 11/1999 | Gabe et al. |
| 5,998,143 A | 12/1999 | Ellis et al. |
| 6,004,744 A | 12/1999 | Goelet et al. |
| 6,013,431 A | 1/2000 | Soderlund et al. |
| 6,013,499 A | 1/2000 | Narumiya et al. |
| 6,017,702 A | 1/2000 | Lee et al. |
| 6,018,041 A | 1/2000 | Drmanac et al. |
| 6,043,031 A | 3/2000 | Koster et al. |
| 6,045,996 A | 4/2000 | Cronin et al. |
| 6,046,005 A | 4/2000 | Ju et al. |
| 6,087,095 A | 7/2000 | Rosenthal et al. |
| 6,110,684 A | 8/2000 | Kemper et al. |
| 6,136,541 A | 10/2000 | Gulati |
| 6,140,054 A | 10/2000 | Wittwer et al. |
| 6,142,681 A | 11/2000 | Gulati |
| 6,143,496 A | 11/2000 | Brown |

(Continued)

FOREIGN PATENT DOCUMENTS

| | | |
|---|---|---|
| CN | 1930303 A | 3/2007 |
| WO | WO 97/35589 | 10/1997 |

(Continued)

OTHER PUBLICATIONS

See New England Biolabs, Inc. 1998/99 Catalog, Beverly, MA, USA pp. 256-257.*
Dhallan et al., "A non-invasive test for prenatal diagnosis based on fetal DNA present in maternal blood: a preliminary study", Lancet, Feb. 20, 2007, vol. 369, pp. 474-481.
Fuery et al., Detection of Rare Mutant Alleles by Restriction Endonuclease-mediated Selective-PCR: Assay Design and Optimization:, Clinical Chemistry, 2000, vol. 46, pp. 620-624.
International Search Report and Written Opinion mailed on: Dec. 18, 2009 in International Application No. PCT/US2009/038304, filed on Mar. 25, 2009.
Sekizawa et al., "Recent advances in non-invasive prenatal DNA diagnosis through maternal blood", J. Obstet. Gynacol. Res, Dec. 2007, vol. 33. No. 6, pp. 747-764.
Hatcher et al., Prenatal Diagnosis by enzymatic amplification and restriction endonuclease digestion for detection of hemoglobins A, S and C, Molecular and Cellular Probes, Academic Press, London. GB. vol. 6, No. 4., Aug. 1, 1992 pp. 343-348.

(Continued)

*Primary Examiner* — James Martinell
(74) *Attorney, Agent, or Firm* — Grant Anderson LLP

(57) ABSTRACT

Provided is an improved method for the detection of specific polymorphic alleles in a mixed DNA population. The method comprises enriching the relative percentage of a given polymorphic allele that is exponentially amplifiable by PCR. Also provided are methods for selectively enriching target nucleic acid, for example, fetal nucleic acid in a maternal sample. In the case of detecting fetal nucleic acid in a maternal sample, a restriction enzyme is introduced that can discriminate between the alleles of a polymorphic site. Preferably, the maternal allele is digested and nucleic acid comprising the paternal allele is relatively enriched.

9 Claims, 12 Drawing Sheets

(56) References Cited

U.S. PATENT DOCUMENTS

| | | | |
|---|---|---|---|
| 6,156,501 | A | 12/2000 | McGall et al. |
| 6,183,958 | B1 | 2/2001 | Stanton, Jr. |
| 6,194,144 | B1 | 2/2001 | Koster |
| 6,197,506 | B1 | 3/2001 | Fodor et al. |
| 6,210,891 | B1 | 4/2001 | Nyren et al. |
| 6,221,601 | B1 | 4/2001 | Koster et al. |
| 6,221,605 | B1 | 4/2001 | Koster |
| 6,223,127 | B1 | 4/2001 | Berno |
| 6,225,625 | B1 | 5/2001 | Pirrung et al. |
| 6,229,911 | B1 | 5/2001 | Balaban et al. |
| 6,239,273 | B1 | 5/2001 | Pease et al. |
| 6,258,538 | B1 | 7/2001 | Koster et al. |
| 6,261,768 | B1 | 7/2001 | Todd et al. |
| 6,268,144 | B1 | 7/2001 | Koster |
| 6,277,573 | B1 | 8/2001 | Koster |
| 6,300,076 | B1 | 10/2001 | Koster |
| 6,602,662 | B1 | 8/2003 | Koster et al. |
| 6,814,934 | B1 | 11/2004 | Higuchi |
| 2001/0031467 | A1 | 10/2001 | Dapprich et al. |
| 2002/0022224 | A1 | 2/2002 | Hornby et al. |
| 2002/0064791 | A1 | 5/2002 | Whitaker et al. |
| 2003/0027135 | A1 | 2/2003 | Ecker et al. |
| 2003/0082539 | A1 | 5/2003 | Ecker et al. |
| 2003/0124556 | A1 | 7/2003 | Ecker et al. |
| 2003/0175695 | A1 | 9/2003 | Ecker et al. |
| 2003/0175696 | A1 | 9/2003 | Ecker et al. |
| 2003/0175697 | A1 | 9/2003 | Ecker et al. |
| 2003/0190605 | A1 | 10/2003 | Ecker et al. |
| 2003/0211522 | A1 | 11/2003 | Landes et al. |
| 2003/0232351 | A1 | 12/2003 | Feinberg |
| 2004/0009518 | A1 | 1/2004 | Lo et al. |
| 2004/0137470 | A1 | 7/2004 | Dhallan |
| 2004/0180328 | A1 | 9/2004 | Ecker et al. |
| 2004/0219517 | A1 | 11/2004 | Ecker et al. |
| 2004/0229224 | A1 | 11/2004 | Frazer |
| 2005/0042639 | A1 | 2/2005 | Knapp et al. |
| 2005/0079521 | A1 | 4/2005 | Beaulieu et al. |
| 2005/0164241 | A1 | 7/2005 | Hahn et al. |
| 2005/0272070 | A1 | 12/2005 | Ehrich et al. |
| 2005/0287592 | A1 | 12/2005 | Kless |
| 2006/0099581 | A1 | 5/2006 | Berlin |
| 2006/0269925 | A1 | 11/2006 | Nunes et al. |
| 2007/0048735 | A1 | 3/2007 | Ecker et al. |
| 2007/0059707 | A1 | 3/2007 | Cantor et al. |
| 2008/0299562 | A1 | 12/2008 | Oeth et al. |
| 2009/0317818 | A1 | 12/2009 | Ehrich et al. |

FOREIGN PATENT DOCUMENTS

| | | |
|---|---|---|
| WO | WO 00/28081 | 5/2000 |
| WO | WO 00/52625 | 9/2000 |
| WO | WO 01/20039 | 3/2001 |
| WO | WO 01/25485 | 4/2001 |
| WO | WO 01/27326 | 4/2001 |
| WO | WO 01/27327 | 4/2001 |
| WO | WO 01/27329 | 4/2001 |
| WO | WO 01/29259 | 4/2001 |
| WO | WO 2005/035725 | 4/2005 |
| WO | WO 2006/056480 | 6/2006 |
| WO | WO 2007/028155 | 3/2007 |
| WO | WO 2007/140417 | 12/2007 |
| WO | WO 2007/147063 | 12/2007 |
| WO | WO 2008/118988 | 10/2008 |
| WO | WO 2008/157264 | 12/2008 |
| WO | WO 2009/032779 | 3/2009 |
| WO | WO 2009/032781 | 3/2009 |

OTHER PUBLICATIONS

Office Action mailed: Apr. 27, 2011 in U.S. Appl. No. 12/411,329, filed Mar. 25, 2009 and published as: 2009/0317818 on: Dec. 24, 2009.
Reference Single Nucleotide Polymorphism rs12007, submitted to NCBI as ss44816763 by ABI, Jul. 19, 2005, pp. 1-13.
Reference Single Nucleotide Polymorphism rs910500, submitted to NCBI as ss5159471 by TSC-CSHL, Sep. 19, 2001, pp. 1-8.
Supplementary European Search Report dated Mar. 3, 2011 in European Application No. EP 08744402.2 filed Mar. 26, 2008.
Weber et al., "A real-time Polymerase chain reaction assay for quantification of allele ratios and correction of amplification bias," Analytical Biochemistry, Academic Press Inc, New York, vol. 320, No. 2, Sep. 15, 2003, pp. 252-258.
Supplementary European Search Report dated: Sep. 1, 2011 in European Application No. EP 09726123 filed: Mar. 26, 2008 based on International Application No. PCT/US2009/038304.
Ausubel, et al., Current protocols in Molecular Biology, Greene Publishing, 1995, pp. i, iii-v, and 1-12.
Boom et al., 1990, J. Clin. Microbiol. 28: 495-503.
Boom et al., 1991, J. Clin. Microbiol. 29: 1804-1811.
Chen & Kwok, *Nucleic Acids Research 25*: 347-353 (1997).
Chen et al., *Proc. Natl. Acad. Sci. USA 94/20*: 10756-10761 (1997).
Cheung et al., 1994, J. Clin. Microbiol. 32: 2593-2597.
Chirgwin et al., 1979, Biochem. 18: 5294-5299.
Chiu et al., 2001, *Clin. Chem.* 47: 1607-1613.
Chomczynski and Mackey, 1995, Anal. Biochem. 225: 163-164.
Chomczynski and Mackey, 1995, Biotechniques 19: 942-945.
Chomczynski and Sacchi, 1987, Analytical Biochem. 162: 156-159.
Chomczynski, 1993, Biotech. 15: 532-537.
Fournie et al.,1986 Anal. Biochem. 158: 250-256.
Grompe et al., *Proc. Natl. Acad. Sci. USA 86*:5888-5892 (1989).
Grompe, *Nature Genetics 5*: 111-117 (1993).
Innis et al., PCR Protocols: A Guide to Methods and Applications, Innis et al., eds, 1990, pp. v-x.
International Search Report and Written Opinion mailed on: Jun. 30, 2008 in International Application No. PCT/US2008/58317, filed on Mar. 26, 2008.
International Preliminary Report on Patentability mailed on: Oct. 8, 2009 in International Application No. PCT/US2008/58317, filed on Mar. 26, 2008.
Jurinke, C., Oeth, P., van den Boom, D., MALDI-TOF mass spectrometry: a versatile tool for high-performance DNA analysis. *Mol. Biotechnol.* 26, 147-164 (2004).
Lo et al. *Am J Hum Genet.* Apr. 1998;62(4):768-775.
Lo et al. *Lancet.* Aug. 16, 1997;350(9076):485-487.
Nasis et al. *Clin Chem.* Apr. 2004;50(4):694-701.
NCBI: Single Nucleotide Polymorphisms rs432950, May 25, 2006, (online), (Retrieved on Jun. 3, 2008), Retrieved from the National Center for Biotechnology Information (at NIH) database using internet: <URL: http:ncbi.nlm.nih.gov/SNP/snp_ref.cgi?type=rs&rs=4329520>.
Oeth, P. et al., iPLEX™ Assay: Increased Plexing Efficiency and Flexibility for MassARRAY® System through single base primer extension with mass-modified Terminators. SEQUENOM Application Note (2005).
Orita et al., *Proc. Natl. Acad. Sci. U.S.A 86*: 2776-2770 (1989).
Poch et al., "Sth132I, a novel class-IIS restriction endonuclease of *Streptococcus thermophilus* ST132" Gene 195: 201-206 (1997).
Sambrook et al., Molecular Biology: A laboratory Approach, Cold Spring Harbor, N.Y. 1989; pp. v-xx.
Sheffield et al., *Proc. Natl. Acad. Sci. USA 49*: 699-706 (1991).
White et al., *Genomics 12*: 301-306 (1992).
Office Action mailed: Feb. 29, 2012 in U.S. Appl. No. 12/411,329, filed Mar. 25, 2009 and published as: US-2009/0317818 on: Dec. 24, 2009.
Office Action mailed on Apr. 3, 2013 in U.S. Appl. No. 13/481,612, filed May 25, 2012 and published as 2012-0270217 on Oct. 25, 2012.
International Preliminary Report on Patentability mailed on Mar. 11, 2010 in International Application No. PCT/US2008/074689, filed on Aug. 28, 2008.
International Search Report and Written Opinion mailed on Mar. 23, 2009 in International Application No. PCT/US2008/074689, filed on Aug. 28, 2008.
International Preliminary Report on Patentability mailed on Oct. 7, 2010 in International Application No. PCT/US2009/038304, filed on Mar. 25, 2009.
International Search Report and Written Opinion mailed on Oct. 9, 2008 in International Application No. PCT/US2007/071232, filed on Jun. 14, 2007.

(56) References Cited

OTHER PUBLICATIONS

International Preliminary Report on Patentability mailed on Mar. 12, 2009 in International Application No. PCT/US2007/071232, filed on Jun. 14, 2007.
Amicucci et al., (2000) Clin Chem 46:301-302.
Anker and Stroun, Clin. Chem. (2002) 48:1210-1211.
Anker et al., Cancer Metastasis Rev. (1999) 18:65-73.
Bischoff et al., Hum. Reprod. Update. Jan.-Feb. 2005;11 (1):59-67.
Chan et al, Clin Chem. Jan. 2004;50(1):88-92.
Chan KC and Lo YM, Histol Histopathol (2002) 17,937-943.
Chen XQ, et al. Nat Med (1996) 2,1033-1035.
Chiu RWK, et al. (2002) Lancet 360:998-1000.
Costa JM, Ernault P (2002) Clin Chem 48:679-680.
Costa JM, et al. Prenat Diagn 21:1070-1074, (2001).
Finning KM, et al. (2002) Transfusion 42:1079-1085.
Fournie et al., Cancer Lett 1995;91:221-227.
Fournie et al., Gerontology 1993;39:215-221.
Fucharoen G, et al. (2003) Prenat Diagn 23:393-396.
Gonzalez-Gonzalez MC, et al. (2002) Prenat Diagn 22:946-948.
Gonzalez-Gonzalez MC, et al. (2003) Prenat Diagn 23:232-234.
Jahr S, et al. Cancer Res (2001) 61,1659-1665.
Li et al, Clin Chem. Jun. 2004;50(6):1002-1011.
Lo et al. (1998) N Engl J Med 339:1734-1738.
Lo et al. Am J Hum Genet (1999) 64:218-224.
Lo KW, et al. Clin Chem (1999) 45,1292-1294.
Lo et al., Lancet 1998;351:1329-1330.
Lo et al., Clin Chem 2000;46:319-323.
Nawroz H et al., Nat Med 1996;2:1035-1037.
Nelson, Crit. Rev. Clin. Lab Sci. (1998) 35(5):369-414.
Ng EK, et al. Proc Natl Acad Sci USA (2003) 100, 4748-4753.
Rijnders RJ, et al. (2001) Obstet Gynecol 98:374-378.
Rumore and Steinman J Clin Invest. Jul. 1990;86(1):69-74.
Saito H, et al. (2000) Lancet 356:1170.
Stroun M, et al. Oncology (1989) 46,318-322.
Wang et al. Clin Chem. Jan. 2004;50(1):211-213.
Widlak et al, J Biol Chem. Mar. 17, 2000;275(11):8226-8232.
Office Action mailed on Oct. 10, 2013 in U.S. Appl. No. 13/481,612, filed on May 25, 2012 and published as 2012-0270217 on Oct. 25, 2012.
Office Action mailed on Nov. 8, 2013 in U.S. Appl.No. 13/481,612, filed on May 25, 2012 and published as 2012-0270217 on Oct. 25, 2012.

* cited by examiner

FIGURE 8A

```
Non-invasive prenatal sex test - AMG_(F/M)-

10        20        30        40        50        60
AM-X.SEQ    ACCTCATCCTGGGCACCCTGGTTATATCAACTTCAGCTATGAGGTAATTTTTCTCTTTAC
            X:::::::::::::::::::::::::::::::::::::::::::::::::::::::::::
AM-Y.SEQ    ACCTCATCCTGGGCACCCTGGTTATATCAACTTCAGCTATGAGGTAATTTTTCTCTTTAC
                    10        20        30        40        50        60

70        80        90       100       110       120
AM-X.SEQ    TAATTTTGACCATTGTTTGCGTTAACAATGCCCTGGGCTCTGTAAAGAATAGTGTGTTGA
            :::::::::: ::  ::::::: :::  :: :  ::::::::::::::::::::: :: ::
AM-Y.SEQ    TAATTTTGATCACTGTTTGCATTAGCAGTCCCCTGGGCTCTGTAAAGAATAGTGGGTGGA
                    70        80        90       100       110       120

130                 140       150       160       170
AM-X.SEQ    TTCTTTATCCCAGAT------GTTTCTCAAGTGGTCCTGATTTTACAGTTCCTACCACCA
            ::::: ::::::X ::      ::::::::::::::::::  :::::::::::::::: ::
AM-Y.SEQ    TTCTTCATCCCAAATAAAGTGGTTTCTCAAGTGGTCCCAATTTTACAGTTCCTACCATCA
                   130       140       150       160       170       180

180       190       200       210
AM-X.SEQ    GCTTCCCAGTTTAAGCTCTGATGGTTGGCCTCAAGCCT
            ::::::::::::::::::::::::::::::::::::::
AM-Y.SEQ    GCTTCCCAGTTTAAGCTCTGATGGTTGGCCTCAAGCCT
                   190       200       210

Primers for non-invasive prenatal sex testing using AMG as target:

PCR primers:
AMG-F:      5'-ACGTTGGATGCCCTGGGCTCTGTAAAGAAT-3'
AMG-R:      5'-ACGTTGGATGAGGCTTGAGGCCAACCATCAG-3'

EXTEND primers:
AMG-E:      5'-TTCTTCATCCCAAATAAAGT-3'

Competitors:
AMG-X-S:
5'-CCCTGGGCTCTGTAAAGAATAGTGTGTTGATTCTTTATCCCAGAaGTTTCTCAAGTGGTCCTGATTTTACAGTTCCTACCACCA
GCTTCCCAGTTTAAGCTCTGATGGTTGGCCTCAAGCCT-3'

AMG-X-AS:
5'-AGGCTTGAGGCCAACCATCAGAGCTTAAACTGGGAAGCTGGTGGTAGGAACTGTAAAATCAGGACCACTTGAGAAACtTCTGGGATAAAGA
ATCAACACACTATTCTTTACAGAGCCCAGGG-3'

AMG-Y-S:
5'-CCCTGGGCTCTGTAAAGAATAGTGGGTGGATTCTTCATCCCAAATAAAGTcGTTTCTCAAGTGGTCCCAATTTTACAGTTCCTACCATCA
GCTTCCCAGTTTAAGCTCTGATGGTTGGCCTCAAGCCT-3'

AMG-Y-AS:
5'- AGGCTTGAGGCCAACCATCAGAGCTTAAACTGGGAAGCTGATGGTAGGAACTGTAAAATTGGGACCACTTGAGAAACgACTTTATTTGGGATGA
AGAATCCACCCACTATTCTTTACAGAGCCCAGGG
```

FIGURE 8B

```
Non-invasive prenatal sex test - AMG-XY-5-i 10        20        30        40        50        60
AM-X.SEQ    ACCTCATCCTGGGCACCCTGGTTATATCAACTTCAGCTATGAGGTAATTTTTCTCTTTAC
            X:::::::::::::::::::::::::::::::::::::::::::::::::::::::::::
AM-Y.SEQ    ACCTCATCCTGGGCACCCTGGTTATATCAACTTCAGCTATGAGGTAATTTTTCTCTTTAC
                 10        20        30        40        50        60

70        80        90       100       110       120
AM-X.SEQ    TAATTTTGACCATTGTTTGCGTTAACAATGCCCTGGGCTCTGTAAAGAATAGTGTGTTGA
            ::::::::::  :: :::::::: :::  :: : :::::::::::::::::::: :: ::
AM-Y.SEQ    TAATTTTGATCACTGTTTGCATTAGCAGTCCCCTGGGCTCTGTAAAGAATAGTGGGTGGA
                 70        80        90       100       110       120

130       140       150       160       170
AM-X.SEQ    TTCTTTATCCCAGAT------GTTTCTCAAGTGGTCCTGATTTTACAGTTCCTACCACCA
            ::::: ::::::X ::         :::::::::::::::: :::::::::::::::: ::
AM-Y.SEQ    TTCTTCATCCCAAATAAAGTGGTTTCTCAAGTGGTCCCAATTTTACAGTTCCTACCATCA
                130       140       150       160       170       180

180       190       200       210
AM-X.SEQ    GCTTCCCAGTTTAAGCTCTGATGGTTGGCCTCAAGCCT
            ::::::::::::::::::::::::::::::::::::::
AM-Y.SEQ    GCTTCCCAGTTTAAGCTCTGATGGTTGGCCTCAAGCCT
                   190       200       210

Primers for non-invasive prenatal sex testing using AMG as target:

PCR primers:
AMG-XY-5-i-F:     5'-ACGTTGGATGTATCAACTTCAGCTATGAGG-3'
AMG-XY-5-i-R:     5'-ACGTTGGATGCACTATTCTTTACAGAGC-3'

EXTEND primers:
AMG-XY-5-i-E:     5'-CTTTACAGAGCCCAGGG-3'

Competitors:
AMG-XY-5-i-S:
5'-TATCAACTTCAGCTATGAGGTAATTTTTCTCTTTACTAATTTTGAYCAYTGTTTGCRTTARCARTaCCCTGGGCTCTGTAAAGAATAGTG-3'

AMG-XY-5-i-AS:
5'-CACTATTCTTTACAGAGCCCAGGGtARTGRTAARGCAAACAYTGYTCAAAATTAGTAAAGAGAAAAATTACCTCATAGCTGAAGTTGATA-3'
```

FIGURE 8C

Non-invasive prenatal sex test

```
                   10        20        30        40        50        60
AM-X.SEQ    ACCTCATCCTGGGCACCCTGGTTATATCAACTTCAGCTATGAGGTAATTTTTCTCTTTAC
            ::::::::::::::::::::::::::::::::::::::::::::::::::::::::::::
AM-Y.SEQ    ACCTCATCCTGGGCACCCTGGTTATATCAACTTCAGCTATGAGGTAATTTTTCTCTTTAC
                   10        20        30        40        50        60

70        80        90       100       110       120
AM-X.SEQ    TAATTTTGACCATTGTTTGCGTTAACAATGCCCTGGGCTCTGTAAAGAATAGTGTGTTGA
            :::::::::: :: ::::::: ::: :: :::::::::::::::::::::::: :: ::
AM-Y.SEQ    TAATTTTGATCACTGTTTGCATTAGCAGTCCCCTGGGCTCTGTAAAGAATAGTGGGTGGA
                   70        80        90       100       110       120

130       140       150       160       170
AM-X.SEQ    TTCTTTATCCCAGAT------GTTTCTCAAGTGGTCCTGATTTTACAGTTCCTACCACCA
            ::::: :::::X ::      :::::::::::::::  ::::::::::::::::::: ::
AM-Y.SEQ    TTCTTCATCCCAAATAAAGTGGTTTCTCAAGTGGTCCCAATTTTACAGTTCCTACCATCA
                   130       140       150       160       170       180

180       190       200       210
AM-X.SEQ    GCTTCCCAGTTTAAGCTCTGATGGTTGGCCTCAAGCCT
            ::::::::::::::::::::::::::::::::::::::
AM-Y.SEQ    GCTTCCCAGTTTAAGCTCTGATGGTTGGCCTCAAGCCT
                   190       200       210
```

New primers for non-invasive prenatal sex testing using AMG as target:

PCR primers:
AMG-F:     5'-CCCTGGGCTCTGTAAAGAAT-3'
AMG-R:     5'-GAGCTTAAACTGGGAAGCTG-3'

EXTEND primers:
AMG-Y:     5'-TTCTTCATCCCAAATAAAGT-3'
AMG-CON:   5'-CCCTGGGCTCTGTAAAGAATAGT-3'

EXTEND products:
Y chromosome:        TTCTTCATCCCAAATAAAGTG
Template positive:   CCCTGGGCTCTGTAAAGAATAGTG

RESULTS TABLE

| Sequence Name | Primer Sequence | No. of Nucleotides | Mass |
|---|---|---|---|
| AMG-Y primer | TTCTTCATCCCAAATAAAGT | 20 | 6011 |
| Ychromosome positive | TTCTTCATCCCAAATAAAGTg | 21 | 6340.2 |
| | | | |
| AMG-CON primer | CTGGGCTCTGTAAAGAATAGT | 21 | 6457.2 |
| template positive | CTGGGCTCTGTAAAGAATAGTg | 22 | 6786.4 |
| | | | |
| SRY primer | caggacagcagtagagca | 18 | 5550.6 |
| SRY extension product | caggacagcagtagagcag | 19 | 5879.8 |

FIGURE 9

Non-invasive prenatal Albumin test

```
Query   1    GCTCAGTATCTTCAGCAGTGTCCATTTGAAGATCATGTAAAATTAGTGAATGAAGTAACT   60
             ||||||||||||||||||||||||||||||||||||||||||||||||||||||||||||
Sbjct 193    GCTCAGTATCTTCAGCAGTGTCCATTTGAAGATCATGTAAAATTAGTGAATGAAGTAACT  252

Query  61    GAATTTGC   68
             ||||||||
Sbjct 253    GAATTTGC  260
```

ALB Assay:

PCR-F: 5'-ACGTTGGATGCAGTATCTTCAGCAGTGTCC-3'

PCR-R: 5'-ACGTTGGATGGCAAATTCAGTTACTTCATTC-3'

Extend: 5'-CAGTGTCCATTTGAAGATC-3'

Competitor-S:
5'-CAGTATCTTCAGCAGTGTCCATTTGAAGATCtTGTAAAATTAGTGAATGAAGTAACTGAATTTGC-3'

Competitor-AS:
5'-GCAAATTCAGTTACTTCATTCACTAATTTTACAaGATCTTCAAATGGACACTGCTGAAGATACTG-3'

RESTRICTION ENDONUCLEASE ENHANCED POLYMORPHIC SEQUENCE DETECTION

RELATED PATENT APPLICATIONS

This patent application is a national stage of international patent application number PCT/US2008/058317, filed on Mar. 26, 2008, which claims the benefit of U.S. provisional patent application No. 60/908,167, filed on Mar. 26, 2007, entitled "RESTRICTION ENDONUCLEASE ENHANCED POLYMORPHIC SEQUENCE DETECTION." The entire content of each of these patent applications hereby is incorporated by reference herein, including all text, drawings and tables, in jurisdictions providing for such incorporation.

SEQUENCE LISTING

The instant application contains a Sequence Listing which has been submitted via EFS-Web and is hereby incorporated by reference in its entirety. Said ASCII copy, created on Dec. 7, 2009, is named SEQ68US.txt, and is 72,183 bytes in size.

FIELD OF THE INVENTION

Provided herein are methods for detecting specific alleles in a mixed nucleic acid sample. The methods can be used to detect the presence or absence of fetal nucleic acid in a maternal sample.

BACKGROUND

The analysis of circulating nucleic acids has revealed applications in the non-invasive diagnosis, monitoring, and prognostication of many clinical conditions. For example, for prenatal applications, circulating fetal-specific sequences have been detected and constitute a fraction of the total DNA in maternal plasma. The diagnostic reliability of circulating DNA analysis depends on the fractional concentration of the targeted sequence, the analytical sensitivity, and the specificity. The robust discrimination of sequence differences (e.g., single-nucleotide polymorphisms, or SNPs) between circulating DNA species is technically challenging and demands the adoption of highly sensitive and specific analytical methods.

Current techniques to detect sequence differences in a DNA sample include allele-specific PCR, restriction digest and Southern blot hybridization, restriction endonuclease-mediated selective-PCR (REMS-PCR), and competitive PCR methods involving the use of fluorescent detection probes. The currently available techniques present several disadvantages. For allele-specific PCR, it is often difficult to design assays with a high degree of allele specificity (Nasis et al. *Clin Chem.* 2004 April; 50(4):694-701). Restriction digest/Southern blot methods require higher amounts of DNA template than the method provided herein, and lack the sensitivity to detect polymorphic sequences comprising a low relative proportion of total DNA. Restriction endonuclease-mediated selective-PCR (REMS-PCR) has the drawback of requiring a thermostable restriction enzyme that cleaves the wild-type allele. REMS-PCR is described in U.S. Pat. No. 6,261,768, which is hereby incorporated by reference. Use of the technique may not always be possible, and this requirement limits the general utility of the REMS-PCR approach. Competitive PCR lacks the sensitivity to detect polymorphic sequences comprising a low relative proportion (<5%) of total DNA. Competitive PCR with allele-specific fluorescent probes lacks the ability to multiplex assays higher than 2-3 assays in a single tube format.

In addition, similar methods utilizing methylation differences between DNA species (for example, US Patent Application Publication No. 20070059707, entitled, "Methods for prenatal diagnosis of chromosomal abnormalities", which is hereby incorporated by reference) are not effective at low copy numbers of genomic DNA.

SUMMARY

The invention in part provides sequence-specific cleavage of nucleic acid to selectively enrich for a particular target nucleic acid. Polymorphic loci are chosen such that only one allele at the polymorphic locus is cleaved by a given cleavage agent, such as a restriction endonuclease. Oligonucleotide primer pairs designed to flank the polymorphism allow amplification of the polymorphic region, or amplicon, by amplification (e.g., PCR). Prior to or during amplification, nucleic acid samples are incubated with the given restriction endonuclease. In a preferred embodiment, the cleavage agent is introduced prior to amplification. This embodiment results in cleavage of the polymorphic allele or sequence comprising the polymorphic allele that is recognized by the restriction endonuclease, if this allele is present. Cleavage of any template nucleic acid within the amplicon sequence (i.e., between primer pairs) prevents PCR amplification of this template. Therefore, if only one allele of a polymorphism is recognized by the cleavage agent and the corresponding nucleic acid sequence is cleaved by the restriction endonuclease, the relative percentage of the amplifiable alternate polymorphic allele is increased in a manner dependent on the efficiency and specificity of the restriction endonuclease activity. After amplification, the amplified polymorphic alleles can be genotyped or otherwise detected or discriminated by any method known in the art (e.g., using Sequenom's MassARRAY® technology or by RT-PCR).

In one embodiment, the invention in part provides a method for detecting the presence or absence of a target allele at a polymorphic locus in a sample, wherein the sample contains nucleic acid, which comprises: cleaving a nucleic acid comprising a non-target allele at or near the polymorphic locus with a cleavage agent that recognizes and cleaves a non-target allele, but not the target allele; amplifying uncleaved nucleic acid but not cleaved nucleic acid; and analyzing the amplification products from the previous step to determine the presence or absence of the target allele. In a related embodiment, the method also comprises first obtaining a sample suspected of comprising nucleic acid with target and non-target alleles. In a preferred embodiment, the method is used to distinguish between two individuals, for example, between a mother and a fetus, wherein the sample comprises both maternal and fetal nucleic acid. Optionally, the method may be used to quantify the target nucleic acid relative to the non-target nucleic acid.

The invention in part provides methods for enriching for target nucleic acid, comprising cleaving nucleic acid comprising a non-target allele with a restriction endonuclease that recognizes the nucleic acid comprising the non-target allele but not the target allele; and amplifying uncleaved nucleic acid but not cleaved nucleic acid, wherein the uncleaved, amplified nucleic acid represents enriched target nucleic acid relative to non-target nucleic acid. In one embodiment, the methods may be utilized to determine the presence or absence of target nucleic acid in a background of non-target nucleic acid. In a related embodiment, the amplification products can be analyzed to diagnose, monitor or prognose a clinical condition. Likewise, the amplification products can be analyzed to assist in the diagnosis, prognosis or monitoring of a clinical condition or chromosomal abnormality. Nucleic acid may be selected such that it comprises an allele having a polymorphic site that is susceptible to selective digestion by a cleavage agent, for example.

The methods are useful for analyzing nucleic acid including, but not limited to, DNA, RNA, mRNA, oligonucleosomal, mitochondrial, epigenetically-modified, single-stranded, double-stranded, circular, plasmid, cosmid, yeast artificial chromosomes, artificial or man-made DNA, including unique DNA sequences, and DNA that has been reverse transcribed from an RNA sample, such as cDNA, and combinations thereof. In one embodiment, the method is used to detect or selectively enrich RNA.

The nucleic acid may also be characterized as target nucleic acid or non-target nucleic acid, wherein target nucleic comprises the target allele and non-target nucleic acid comprises the non-target allele. In one embodiment, the target nucleic acid comprises the paternal allele and the non-target nucleic acid comprises the maternal allele. In certain embodiments, the nucleic acid is cell-free nucleic acid or partially cell-free nucleic acid. In certain embodiments, the target nucleic acid is apoptotic or partially apoptotic. In certain embodiments, the target nucleic acid is less than 2000, 1200, 1100, 1000, 900, 800, 700, 600, 500, 400, 300, 200, 100, 80, 70, 60, 50, 40 or less base pairs in length.

The methods may be used to detect target nucleic acid in a biological sample. Preferably, the biological sample is from an animal, preferably a human. In a related embodiment, the biological sample is selected from the group of whole blood, serum, plasma, umbilical cord blood, chorionic villi, amniotic fluid, cerbrospinal fluid, spinal fluid, lavage fluid, biopsy sample, urine, feces, sputum, saliva, nasal mucous, prostate fluid, semen, lymphatic fluid, bile, tears, sweat, breast milk, breast fluid, embryonic cells and fetal cells, and mixture thereof. In one embodiment, the sample is from a crime scene (e.g., used for forensic analysis). In certain embodiments, the biological sample is obtained through non-invasive means, for example, a blood draw from a pregnant female. In another preferred embodiment, the biological sample is cell-free. In certain embodiments, the sample is a previously isolated sample of nucleic acids.

In one embodiment, the invention in part provides a method for detecting the presence or absence of fetal nucleic acid in a maternal sample, wherein the sample contains nucleic acid, which comprises: cleaving nucleic acid comprising a maternal allele with a restriction endonuclease that recognizes and cleaves the nucleic acid comprising the maternal allele but not the paternal allele; amplifying uncleaved nucleic acid but not cleaved nucleic acid; and analyzing the amplification products from the previous step to determine the presence or absence of fetal nucleic acid. In certain embodiments, the sample comprises a mixture of nucleic acids. For example, the mixture may comprise nucleic acid from different species or from different individuals. In one embodiment, the sample is from a pregnant female. Samples can be collected from human females at 1-4, 4-8, 8-12, 12-16, 16-20, 20-24, 24-28, 28-32, 32-36, 36-40, or 40-44 weeks of fetal gestation, and preferably between 5-28 weeks of fetal gestation. In certain embodiments, the methods may be used to detect the presence or absence of fetal Y-chromosome nucleic acid, thereby determining the sex of the fetus.

In certain embodiments, the target nucleic acid comprises a paternal allele. In certain embodiments, the mother is homozygous at the polymorphic site and the fetus is heterozygous at the polymorphic site. In the case when the mother is homozygous at the polymorphic site and the fetus is heterozygous at the polymorphic site, the polymorphic site is considered informative (see FIG. 5A for examples of informative and non-informative cases). In a related embodiment, the maternal genotype is determined in conjunction with the methods provided herein. In a related embodiment, the mother is first genotyped (for example, using peripheral blood mononuclear cells (PBMC) from a maternal whole blood sample) to determine the non-target allele that will be recognized and cleaved by the cleavage agent. When the method is used for forensic purposes, the victim may be first genotyped to determine the non-target allele that will be recognized and cleaved by the cleavage agent. Likewise, when used for organ transplant-related applications, the transplant recipient may be first genotyped to determine the non-target allele that will be recognized and cleaved by the cleavage agent.

In some embodiments, the sample contains nucleic acid from two different individuals. Such instances include, but are not limited to, organ transplant recipients, transfusion recipients, and forensic applications.

In certain embodiments, the sample is from an individual suspected of suffering from a disease, and the non-target allele is a wild-type allele that is selectively cleaved in order to enrich for a disease-related point mutation. In a related embodiment, the disease is cancer. The ras proto-oncogenes, K-ras, N-ras, and H-ras, and the p53 tumour suppressor gene are examples of genes which are frequently mutated in human cancers. Specific mutations in these genes leads to activation or increased transforming potential.

The invention in part provides methods useful for detecting rare alleles or low copy number alleles. In one embodiment, the target allele is undetectable by conventional or unmodified genotyping methods if the non-target allele is not selectively cleaved. In a related embodiment, the target allele is not detectable unless it is selectively enriched, for example, by the methods provided herein. In certain embodiments, the target allele concentration (e.g., allele concentration in a sample) is less than 0.5%, 1%, 2%, 3%, 4%, 5%, 6%, 7%, 8%, 9%, 10% 20%, 25%, 30% relative to the non-target allele concentration. In certain embodiments, the target nucleic acid number is less than 5, 6, 7, 8, 9, 10, 11, 12, 13, 14, 15, 16, 17, 18, 19, 20, 25, 30, 35, 40, 50, 55, 60, 70, 80, 90, 100, 150, 200, 250, 300, 400, 500, 600, 700, 800, 900 or 1000. In certain embodiments, the target allele is a mutation, and the non-target allele is the wild-type allele. In a related embodiment, the target allele may be either a somatic or germline mutation. In certain embodiments, another allele or sequence identifier in the same amplicon as the polymorphic locus may be detected. For example, a sequence comprising a target allele may be selectively enriched using the methods provided herein, and another sequence identifier may be detected by any method known in the art.

In some embodiments, there are no other polymorphic loci within the amplicon that may be recognized by the cleavage agent.

In certain embodiments, the method optionally comprises first isolating nucleic acid from the sample. DNA isolation from blood, plasma, or serum of the pregnant mother can be performed using any method known to one skilled in the art. Any standard DNA isolation technique can be used to isolate the fetal DNA and the maternal DNA including, but not limited to, QIAamp DNA Blood Midi Kit supplied by QIAGEN. Other standard methods of DNA isolation are described, for example, in (Sambrook et al., Molecular Biology: A laboratory Approach, Cold Spring Harbor, N.Y. 1989;

Ausubel, et al., Current protocols in Molecular Biology, Greene Publishing, Y, 1995). A preferred method for isolation of plasma DNA is described in Chiu et al., 2001, *Clin. Chem.* 47: 1607-1613, which is herein incorporated by reference in its entirety. Other suitable methods are provided in Example 2 of PCT International Application Publication Number 2007/028155, filed on Sep. 1, 2006.

Methods described herein allow for the use of any cleavage agent capable of distinguishing between two different sequences, and cleaving within the amplicon sequence, thereby preventing amplification of the cleaved sequence. The difference between the sequences may be the result of different alleles at one or more polymorphic sites within the sequence. In another example, the difference between the sequences may be the result of two homologous sequences, for example, between paralogous genes or between highly homologous genes such as the RhD gene, which encodes the D polypeptide, and the RHCE gene, which encodes the CcEe polypeptide. An example of a cleavage agent is a restriction enzyme, also referred to as a restriction endonuclease. Multiple restriction endonucleases (available from various vendors) may be selected that correspond to appropriate sequence differences. In a preferred embodiment, the restriction enzyme is HpyCH4V. In another preferred embodiment restriction enzyme Tsp509I. In certain embodiments, a step is added to end the cleaving activity of the cleavage agent, for example, by introducing a protease and/or high temperature prior to amplification.

The restriction endonuclease may be added prior to or during amplification. In one embodiment, the restriction endonuclease is added less than 5 minutes, 5 minutes, 10 minutes, 20 minutes, 30 minutes, 40 minutes, 50 minutes, 60 minutes, 90 minutes or 120 or more minutes before amplification. Incubation time may be shortened if additional units of restriction enzyme are added to the reaction. Conversely, longer incubation times are often used to allow a reaction to proceed to completion with fewer units of enzyme. This is contingent on how long a particular enzyme can survive (maintain activity) in a reaction. Some enzymes survive for long periods (>16 hours) while others survive only an hour or less in a reaction. In certain embodiments, the restriction enzyme digests greater than 40%, 50%, 60%, 70%, 80%, 90%, 91%, 92%, 93%, 94%, 95%, 96%, 97%, 98% or 99% of the non-target nucleic acid. However, if digestion of non-target nucleic acid of less than 40% allows for useful enrichment of target nucleic acid, it is within the scope of the invention. In certain embodiments, the restriction enzyme digests substantially all of the non-target nucleic acid. In certain embodiments, when the restriction endonuclease is added during amplification, the restriction endonuclease is a thermostable restriction endonuclease which retains activity during thermocycling. Examples of thermostable endonucleases include, but are not limited to, Bst NI, Bsl I, Tru 9I and Tsp 509 I. In certain embodiments, the cleavage agent is not thermostable (non-thermostable), especially when it is preferred that the digestion occurs prior to the amplification step. In a preferred embodiment, the cleavage agent is not thermostable and digestion of the non-target nucleic acid occurs prior to the amplification step. In certain embodiments, a step is introduced to prevent or to reduce digestion during the amplification step.

In one embodiment, the units of restriction enzyme added to the sample is 0.10, 0.25, 0.50, 0.75, 1.0, 2.0 or more. Note that DNA substrates are digested at varying rates, therefore, the actual number of units required for a complete or substantially complete digestion may vary from assay to assay.

In certain embodiments, only one restriction endonuclease is used to digest one or more non-target alleles in a single reaction. For example, a multiplexed assay may be designed wherein a single restriction endonuclease performs multiple (e.g., greater than 5, 10, 15, 20, 25, 50, 100) digestions across the genome. In certain embodiments, more than one restriction endonuclease (e.g., greater than or equal to 2, 3, 4, 5, 6, 7, 8, 9, 10) is used to make multiple (e.g., greater than 5, 10, 15, 20, 25, 50, 100) digestions across the genome.

Amplification may be performed after or during the cleavage of the non-target allele, and prior to the detection of the target allele. In a preferred embodiment, amplification is performed after cleavage of the non-target allele. Amplification can be performed by any method known in the art, including but not limited to polymerase chain reaction (PCR), ligase chain reaction, transcription-based amplification, restriction amplification, or rolling circle amplification, using primers that anneal to the selected fetal DNA regions. In the case that amplification requires thermocycling, cycling greater than 90° C. may be performed such that the cleavage agent is inactivated. Oligonucleotide primers are selected such that they anneal to the sequence to be amplified. In one embodiment, primers are designed such that one or both primers of the primer pair contain sequence recognizable by one or more restriction endonucleases.

Following amplification, the relative enrichment of the target allele in the sample allows accurate detection of allele frequencies using practically any method of nucleic acid detection known in the art. For example, any of the following methods may be used, including, but not limited to, primer extension or microsequencing methods, ligase sequence determination methods, mismatch sequence determination methods, microarray sequence determination methods, restriction fragment length polymorphism (RFLP) procedures, PCR-based assays (e.g., TAQMAN® PCR System (Applied Biosystems)), nucleotide sequencing methods, hybridization methods, conventional dot blot analyses, single strand conformational polymorphism analysis (SSCP), denaturing gradient gel electrophoresis (DGGE), heteroduplex analysis, mismatch cleavage detection, detection by mass spectrometry, real time-PCR and pyrosequencing.

The methods may also be multiplexed at high levels in a single reaction. For example, one or more alleles can be detected simultaneously. Multiplexing embodiments are particularly important when the genotype at a polymorphic locus is not known. In some instances, for example when the mother is heterozygous at the polymorphic locus, the assay may not be informative. See FIG. 5A, which further describes the use of polymorphic variants to detect fetal nucleic acid from a maternal sample. In one embodiment, greater than 1, 2, 3, 4, 5, 6, 7, 8, 9, 10, 11, 12, 13, 14, 15, 16, 17, 18, 19, 20, 25, 30, 35, 40, 50, 60, 70, 80, 90, 100, 200, 300, 500 or more target alleles are assayed, wherein not every target allele is informative. In certain embodiments, the genotype at the polymorphic locus is known. In some embodiments, greater than 1, 2, 3, 4, 5, 6, 7, 8, 9, 10, 11, 12, 13, 14, 15, 16, 17, 18, 19, 20, 25, 30, 35, 40, 50 or more informative target alleles are assayed. The invention also in part includes combinations of different multiplex schemes provided herein.

In certain embodiments, the invention in part provides a method for quantifying a target allele at a polymorphic locus in a sample, wherein the sample contains nucleic acid, that comprises: digesting nucleic acid containing a maternal allele at the polymorphic locus with an enzyme, such as a restriction endonuclease, that selectively digests the maternal allele, wherein the selective digestion yields a DNA sample enriched for fetal DNA; determining the maternal or paternal allele frequency using polymorphic markers within the amplicon, and comparing the paternal or maternal allele frequency to a control DNA sample. In one embodiment, a difference in allele frequency is indicative of a chromosomal abnormality. In certain embodiments, the control DNA sample is a competitor oligonucleotide that is introduced to the assay in known quantities.

In certain embodiments, the present invention in part provides a kit for detecting the presence or absence of target nucleic acid. One component of the kit is primers for amplifying the region of interest. Another component of the kit comprises probes for discriminating between the different alleles of each nucleic acid species.

BRIEF DESCRIPTION OF THE FIGURES

FIGS. 8A-8C provide the location design of the AMG primers. The amplification primers are underlined once and the extend primers are underlined twice. In addition, competitor sequences are provided. Competitor sequences may be used for quantitative methods. FIG. 8C includes a Results Table that shows the different masses generated by each of the AMG and SRY assays, which may be used to interpret the results from the assays. FIG. 8A discloses SEQ ID NOS 275-283, respectively, in order of appearance. FIG. 8B discloses SEQ ID NOS 284-290, respectively, in order of appearance. FIG. 8C discloses SEQ ID NOS 291-294, 279, 295-297, 279, 296, 298-301, respectively in order of appearance.

FIG. 9 provides the location design of the albumin (ALB) primers. The amplification primers are highlighted and the extend primer is underlined twice. Where the PCR primers are provided alone, the sequence-specific portion of the primer is underlined, and the multiplex tag is not underlined. In addition, competitor sequences are provided. Competitor sequences may be used for quantitative methods. FIG. 9 discloses SEQ ID NOS 302 and 302-307, respectively, in order of appearance.

DETAILED DESCRIPTION

Figure 1:
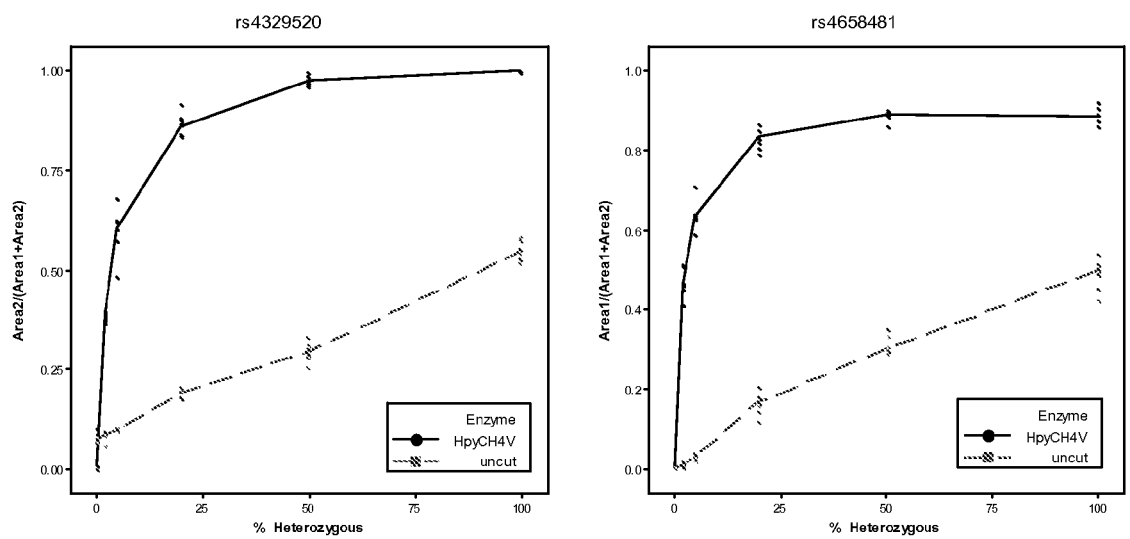
FIG. 1 is the HpyCH4V digest, which shows allele peak area ratios in a DNA mixture series. Peak area ratio is determined by dividing the calculated peak area of the SNP allele not recognized by HpyCH4V (i.e., target allele) by the total peak area of both SNP alleles present in the mass spectrum.

It has been determined in the fields of biology and diagnostics that certain nucleic acids are present at very low concentrations in humans. In particular, fetal DNA has been found to exist in maternal plasma (Lo et al. *Lancet.* 1997 Aug. 16; 350(9076):485-7). This discovery has facilitated the development of non-invasive prenatal diagnostic approaches based simply on the analysis of a maternal blood sample (Lo et al. *Am J Hum Genet.* 1998 April; 62(4):768-75). The non-invasive nature of maternal plasma-based approaches represents a major advantage over conventional methods of prenatal diagnosis, such as amniocentesis and chorionic villus sampling, which are associated with a small but finite risk of fetal loss. However, a technical challenge experienced by many workers in the field relates to the ability to discriminate the relatively small amount of fetal DNA from the coexisting background of maternal DNA in maternal plasma. During pregnancy, fetal DNA amounts to approximately 3-6% of the total DNA in maternal plasma. Hence, the diagnostic reliability of fetal DNA analysis in maternal plasma generally has depended on the accurate detection of fetal-specific markers.

Methods described herein solve this problem by enriching, relatively, the amount of low copy number nucleic acid before detecting or quantifying the alleles present in the sample. In the case of prenatal diagnostics, the use of restriction endonuclease enhanced polymorphic sequence detection allows for the selective, sensitive detection of fetal nucleic acid from maternal samples. The fetal DNA in the maternal plasma sample is selectively enriched before detecting the alleles present in the maternal sample. To enrich for fetal DNA present in plasma of the mother to allow accurate detection of fetal alleles present in the sample, the methods described herein allow for the cleavage of maternal nucleic acid or nucleic acid of maternal origin. Thus, the maternal DNA can be substantially reduced, masked, or destroyed completely, and the sample is left with DNA enriched for DNA of fetal origin. The selective reduction of maternal DNA can be performed using one or more enzymes, such as restriction endonucleases, which selectively digest nucleic acids which comprise maternal alleles.

DEFINITIONS

The term "sample" as used herein includes a specimen or culture (e.g., microbiological cultures) that includes nucleic acids. The term "sample" is also meant to include both biological and environmental samples. A sample may include a specimen of synthetic origin. Biological samples include whole blood, serum, plasma, umbilical cord blood, chorionic villi, amniotic fluid, cerbrospinal fluid, spinal fluid, lavage fluid (e.g., bronchoalveolar, gastric, peritoneal, ductal, ear, athroscopic), biopsy sample, urine, feces, sputum, saliva, nasal mucous, prostate fluid, semen, lymphatic fluid, bile, tears, sweat, breast milk, breast fluid, embryonic cells and fetal cells. The biological sample can be maternal blood, including maternal plasma or serum. In some circumstances, the biological sample is acellular. In other circumstances, the biological sample does contain cellular elements or cellular remnants in maternal blood.

In a preferred embodiment, the sample comprises a mixture of nucleic acids. For example, the mixture may comprise nucleic acid from different species or from different individuals. In one embodiment, the sample is from a pregnant female or a female suspected of being pregnant. In a related embodiment, the sample is procured through non-invasive means (e.g., a blood draw). In certain embodiments the sample is from any animal, including but not limited, human, non-human, mammal, reptile, cattle, cat, dog, goat, swine, pig, monkey, ape, gorilla, bull, cow, bear, horse, sheep, poultry, mouse, rat, fish, dolphin, whale, and shark, or any animal or organism that may be tested for the presence of target nucleic acid.

In a preferred embodiment, the biological sample is blood, and more preferably plasma. As used herein, the term "blood" encompasses whole blood or any fractions of blood, such as serum and plasma as conventionally defined. Blood plasma refers to the fraction of whole blood resulting from centrifugation of blood treated with anticoagulants. Blood serum refers to the watery portion of fluid remaining after a blood sample has coagulated. Environmental samples include environmental material such as surface matter, soil, water, crime scene samples, and industrial samples, as well as samples obtained from food and dairy processing instruments, apparatus, equipment, utensils, disposable and non-disposable items. These examples are not to be construed as limiting the sample types applicable to the present invention.

The term "non-invasive" as used herein refers a method for collecting a sample that poses minimal risk to an individual (e.g., the mother, fetus, victim, etc.). An example of a non-invasive method is a blood draw; whereas examples of invasive methods include amniocentesis and chorionic villus sampling, both of which constitute a finite risk to the fetus.

The terms "target" or "target nucleic acid" as used herein are intended to mean any molecule whose presence is to be detected or measured or whose function, interactions or properties are to be studied, wherein target nucleic comprises the target allele and non-target nucleic acid comprises the non-target allele. Fetal nucleic acid may comprise both target nucleic acid and non-target nucleic when the fetus is heterozygous at a polymorphic locus. Other examples of target nucleic acid include, but are not limited to, trace nucleic acid, mutated nucleic acid, viral nucleic acid and transplant nucleic acid.

The terms "nucleic acid" and "nucleic acid molecule" may be used interchangeably throughout the disclosure. The terms refer to oligonucleotides, oligos, polynucleotides, deoxyribonucleotide (DNA), genomic DNA, mitochondrial DNA (mtDNA), complementary DNA (cDNA), bacterial DNA, viral DNA, viral RNA, RNA, message RNA (mRNA), transfer RNA (tRNA), ribosomal RNA (rRNA), siRNA, catalytic RNA, clones, plasmids, M13, P1, cosmid, bacteria artificial chromosome (BAC), yeast artificial chromosome (YAC), amplified nucleic acid, amplicon, PCR product and other types of amplified nucleic acid, RNA/DNA hybrids and polyamide nucleic acids (PNAs), all of which can be in either single- or double-stranded form, and unless otherwise limited, would encompass known analogs of natural nucleotides that can function in a similar manner as naturally occurring nucleotides and combinations and/or mixtures thereof. Thus, the term "nucleotides" refers to both naturally-occurring and modified/non-naturally-occurring nucleotides, including nucleoside tri, di, and monophosphates as well as monophosphate monomers present within polynucleic acid or oligonucleotide. A nucleotide may also be a ribo; 2'-deoxy; 2',3'-deoxy as well as a vast array of other nucleotide mimics that are well-known in the art. Mimics include chain-terminating nucleotides, such as 3'-O-methyl, halogenated base or sugar substitutions; alternative sugar structures including nonsugar, alkyl ring structures; alternative bases including inosine; deaza-modified; chi, and psi, linker-modified; mass label-modified; phosphodiester modifications or replacements including phosphorothioate, methylphosphonate, boranophosphate, amide, ester, ether; and a basic or complete internucleotide replacements, including cleavage linkages such a photocleavable nitrophenyl moieties.

In the case of RNA, the RNA may be placentally-expressed RNA in maternal plasma. Background maternal RNA may be selectively digested according to the methods provided herein. Also, the method may further comprise the additional step of discriminating the alleles of RNA which involves reverse transcriptase polymerase chain reaction (RT-PCR). In certain embodiments, the fetal RNA may be extracted from maternal body fluids, preferably whole blood, and more preferably plasma or serum using e.g. RNA extraction methods such as, but not limited to, gelatin extraction method; silica, glass bead, or diatom extraction method; guanidinium thiocyanate acid-phenol based extraction methods; guanidinium thiocyanate acid based extraction methods; guanidine-hydrochloride based extraction methods; methods using centrifugation through cesium chloride or similar gradients; phenol-chloroform based extraction methods; and/or other available RNA extraction methods, as are known in the art for use in extraction of intracellular RNA, including commercially available RNA extraction methods, e.g. by using or adapting or modifying the methods of Boom et al. (1990, J. Clin. Microbiol. 28: 495-503); Cheung et al. (1994, J. Clin. Microbiol. 32: 2593-2597); Boom et al. (1991, J. Clin. Microbiol. 29: 1804-1811); Chomczynski and Sacchi (1987, Analytical Biochem. 162: 156-159); Chomczynski, (1993, Biotech. 15: 532-537); Chomczynski and Mackey (1995, Biotechniques 19: 942-945); Chomczynski and Mackey (1995, Anal. Biochem. 225: 163-164); Chirgwin et al. (1979, Biochem. 18: 5294-5299); Fournie et al. (1986 Anal. Biochem. 158: 250-256); and WO97/35589.

The term "amplification reaction" refers to any in vitro means for multiplying the copies of nucleic acid.

"Amplifying" refers to a step of submitting a sample to conditions sufficient to allow for amplification. Components of an amplification reaction may include, but are not limited to, e.g., primers, a polynucleotide template, polymerase, nucleotides, dNTPs and the like. The term "amplifying" typically refers to an "exponential" increase in target nucleic acid. However, "amplifying" as used herein can also refer to linear increases in the numbers of a select target sequence of nucleic acid, but is different than a one-time, single primer extension step.

"Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990.

"Oligonucleotide" as used herein refers to linear oligomers of natural or modified nucleosidic monomers linked by phosphodiester bonds or analogs thereof. Oligonucleotides include deoxyribonucleosides, ribonucleosides, anomeric forms thereof, peptide nucleic acids (PNAs), and the like, capable of specifically binding to a target nucleic acid. Usually monomers are linked by phosphodiester bonds or analogs thereof to form oligonucleotides ranging in size from a few monomeric units, e.g., 3-4, to several tens of monomeric units, e.g., 40-60. Whenever an oligonucleotide is represented by a sequence of letters, such as "ATGCCTG," it will be understood that the nucleotides are in 5'-3' order from left to right and that "A" denotes deoxyadenosine, "C" denotes deoxycytidine, "G" denotes deoxyguanosine, "T" denotes deoxythymidine, and "U" denotes the ribonucleoside, uridine, unless otherwise noted. Oligonucleotides often comprise the four natural deoxynucleotides; however, they may also comprise ribonucleosides or non-natural nucleotide analogs. Where an enzyme has specific oligonucleotide or polynucleotide substrate requirements for activity, e.g., single stranded DNA, RNA/DNA duplex, or the like, then selection of appropriate composition for the oligonucleotide or polynucleotide substrates is well within the knowledge of one of ordinary skill.

As used herein "oligonucleotide primer", or simply "primer", refers to a polynucleotide sequence that hybridizes to a sequence on a nucleic acid template and facilitates the amplification of the nucleic acid template, or otherwise plays a role in the detection of the nucleic acid molecule. In amplification embodiments, an oligonucleotide primer serves as a point of initiation of nucleic acid synthesis. Primers can be of a variety of lengths and are often less than 50 nucleotides in length, for example 12-25 nucleotides, in length. The length and sequences of primers for use in PCR can be designed based on principles known to those of skill in the art.

The term "template" refers to any nucleic acid molecule that can be used for amplification in the methods described herein. RNA or DNA that is not naturally double stranded can be made into double stranded DNA so as to be used as template DNA. Any double stranded DNA or preparation containing multiple, different double stranded DNA molecules can be used as template DNA to amplify a locus or loci of interest contained in the template DNA.

The term "amplicon" as used herein refers to amplified DNA that has been "copied" once or multiple times, e.g. by polymerase chain reaction. The amplicon sequence falls between the amplification primers.

The term "polymorphic locus" as used herein refers to a nucleic acid region that comprises a polymorphism. The nucleic acid region may be 1, 2, 3, 4, 5, 6, 7, 8, 9, 10, 11, 12, 13, 14, 15, 20, 25, 30, 35, 40, 50, 60, 70, 80, 90, 100, 200, 300, 400, 500 or more nucleotides in length.

The term "polymorphism" as used herein refers to an allelic variant. Polymorphisms can include single nucleotide polymorphisms (SNP's) as well as simple sequence length polymorphisms. A polymorphism can be due to one or more nucleotide substitutions at one allele in comparison to another allele or can be due to an insertion or deletion, duplication, inversion and other alterations known to the art. Other polymorphisms include, but are not limited to, restriction fragment length polymorphisms (RFLPs), insertions/deletions, short tandem repeats, such as di-, tri- or tetra-nucleotide repeats (STRs), and the like. As used herein, polymorphism may include epigenetic variants, as long as cleavage by non-epigenetic-specific cleavage agents is used.

The term "allele" as used herein is one of several alternate forms of a gene or non-coding regions of DNA that occupy the same position on a chromosome. The term allele can be used to describe DNA from any organism including but not limited to bacteria, viruses, fungi, protozoa, molds, yeasts, plants, humans, non-humans, animals, and archeabacteria.

Alleles can have the identical sequence or can vary by a single nucleotide or more than one nucleotide. With regard to organisms that have two copies of each chromosome, if both chromosomes have the same allele, the condition is referred to as homozygous. If the alleles at the two chromosomes are different, the condition is referred to as heterozygous. For example, if the locus of interest is SNP X on chromosome 1, and the maternal chromosome contains an adenine at SNP X (A allele) and the paternal chromosome contains a guanine at SNP X (G allele), the individual is heterozygous A/G at SNP X.

As used herein, the term "mutant alleles" may refer to variant alleles that are associated with a disease state, e.g., cancer.

The term "sequence identifier" as used herein refers to any sequence difference that exists between two sequences that can be used to differentiate the sequences. In one embodiment, the sequence identifier does not include methylation differences.

As used herein, the term "genotype" refers to the identity of the alleles or non-homologous variants present in an individual or sample. The term "genotyping a sample" or "genotyping an individual" refers to determining a specific allele or specific nucleotide(s) or polymorphism(s) in a sample or carried by an individual at particular region(s).

The term "selectively" as used herein is not intended to suggest an absolute event, but instead a preferential event. For example, "selectively cleaved" is used to indicate one sequence (for example, the non-target sequence) is preferentially cleaved or digested over another sequence (for example, the target sequence). However, some of the target sequence may also be cleaved due to a lack of specificity with the cleavage agent or other variables introduced during the cleavage process.

The term "cleavage agent" as used herein refers to any means that is capable of differentially cleaving two or more sequences based on a sequence difference that exists between the two or more sequences. The cleavage agent may be an enzyme. The cleavage agent may be natural, synthetic, unmodified or modified. In a preferred embodiment, the cleavage agent is a restriction endonuclease. Restriction endonucleases, alternatively called restriction enzymes, are a class of bacterial enzymes that cut or digest DNA at specific sites. Type I restriction endonucleases occur as a complex with the methylase and a polypeptide that binds to the recognition site on DNA. They are often not very specific and cut at a remote site. Type II restriction endonucleases are the classic experimental tools. They have very specific recognition and cutting sites. The recognition sites are short, 4-8 nucleotides, and are usually palindromic sequences. Because both strands have the same sequence running in opposite directions the enzymes make double-stranded breaks, which, if the site of cleavage is off-center, generates fragments with short single-stranded tails; these can hybridize to the tails of other fragments and are called sticky ends. They are generally named according to the bacterium from which they were isolated (first letter of genus name and the first two letters of the specific name). The bacterial strain is identified next and multiple enzymes are given Roman numerals. For example the two enzymes isolated from the R strain of *E. coli* are designated Eco RI and Eco RII. In a preferred embodiment, the restriction enzyme is a type II restriction endonuclease. In another preferred embodiment, the restriction enzyme is non-thermostable.

The term "chromosomal abnormality" as used herein refers to a deviation between the structure of the subject chromosome and a normal homologous chromosome. The term "normal" refers to the predominate karyotype or banding pattern found in healthy individuals of a particular species. A chromosomal abnormality can be numerical or structural, and includes but is not limited to aneuploidy, polyploidy, inversion, a trisomy, a monosomy, duplication, deletion, deletion of a part of a chromosome, addition, addition of a part of chromosome, insertion, a fragment of a chromosome, a region of a chromosome, chromosomal rearrangement, and translocation. A chromosomal abnormality can be correlated with presence of a pathological condition or with a predisposition to develop a pathological condition.

Uses and Advantages Associated with the Methods Described Herein

The invention in part provides nucleic acid-based assays that are particularly useful for non-invasive prenatal testing. The methods provided herein may be used, inter alia, to determine the presence of fetal nucleic acid in a sample, to determine the amount of fetal nucleic acid in a sample, to determine the sex of a fetus, and to enrich for a target nucleic acid sequence. The invention in part may be combined with other prenatal methods, such as those described in U.S. application Ser. No. 12/027,954, filed Feb. 7, 2008; PCT Application No. PCT/US07/69991, filed May 30, 2007; PCT Application No. PCT/US07/071,232, filed Jun. 15, 2007; U.S. Provisional Application No. 61/033,343, filed Mar. 3, 2008; U.S. Provisional Application No. 61/035,711, filed Mar. 11, 2008; or any of the prenatal diagnostic (both invasive and non-invasive) methods disclosed in U.S. Provisional Application No. 60/944,331, filed Jun. 15, 2007, all of which are hereby incorporated by reference.

The invention in part may be used to more accurately detect fetal DNA using high frequency polymorphisms that match the criteria provided herein. These polymorphisms are alternatively called fetal identifiers. The criteria includes one or more of the following:
1) One allele of the SNP is recognized by the cleavage agent;
2) The alternate SNP allele is not recognized by the same cleavage agent;
3) No other sites for the cleavage are found +/−50 base pair of the SNP within the PCR amplicon; and
4) (Optionally) The minor allele frequency is greater than 0.4 (preferably across a range of populations).

Examples of fetal identifiers are set forth in Tables 6, 9, 10 and 11. In one embodiment, the method of detecting the presence or absence of fetal nucleic acid in a sample comprises obtaining or possessing a nucleic acid sample known to be of maternal origin and suspected of comprising fetal nucleic acid; analyzing the nucleic acid sample to determine the maternal genotype at one or more nucleotide polymorphisms selected from the group consisting of the polymorphisms set forth in Tables 6, 9, 10 and 11; and analyzing the nucleic acid sample to determine the fetal genotype of one or more nucleotide polymorphisms selected from the group consisting of the polymorphisms set forth in Tables 6, 9, 10 and 11, wherein a fetal genotype possessing a paternally-inherited allele indicates the presence of fetal nucleic acid, further wherein nucleic acid comprising a maternal allele is digested using the methods provided herein. In a preferred embodiment, one or more of the polymorphisms set forth in Table 6 or 11 are used in conjunction with the methods provided herein. In a related embodiment, the maternal genotypes are first determined from DNA that is substantially free of fetal nucleic acid. For example, in the case when the sample is blood, the maternal genotypes may be determined from the portion of the blood that comprises nucleated maternal cells (e.g., white blood cells). In one embodiment, the DNA that is substantially free of fetal nucleic acid is from peripheral blood mononuclear cells. In certain embodiments, the amount of fetal DNA is determined by comparing the relative amount of paternally-inherited alleles to an internal control (e.g., competitor oligonucleotide).

In Tables 6, 9, 10 and 11, each primer of the amplification primer pair may comprise the entire sequence shown or only the non-underlined sequence, wherein the underlined portion of the primer is a tag sequence (ACGTTGGATG (SEQ ID NO: 1)) for improved multiplexing and the non-underlined portion is a sequence-specific primer sequence. The tag sequence may be any tag sequence known in the art that improves multiplexing. In certain embodiments, the invention in part includes primers that are substantially similar to the primers provided herein, for example, about 90% or more similar, and further wherein the primers are still specific for a given nucleic acid region. For example, one or more bases of a primer sequence may be changed or substituted, for example with an inosine, but the primer still maintains the same specificity and plexing ability. Bases indicated by uppercase text are complementary to the nucleic acid sequence to which the primer hybridizes, and bases indicated by lowercase text are not complementary to the nucleic acid sequence to which the primer hybridizes. Bases indicated in lower case text can be selected to shift or adjust the mass of primers and amplification products.

In particular embodiments, a sequence tag is attached to a plurality of primary and secondary primer pairs provided in Tables 6, 9, 10 and 11. The sequence tag can be attached to either one or both of the primary and secondary primers from each pair. Typically, the sequence tag is attached to the primary and secondary primer of each pair. The sequence tags used herein can range from 5 up to 20, from 5 up to 30, from 5 up to 40, or from 5 up to 50 nucleotides in length, with a sequence tag of 10-mer length being particularly useful in the methods provided herein. The sequence tag need not be the same sequence for each primer pair in the multiplexed amplification reaction, nor the same sequence for a primary and secondary primer within a particular amplification pair. In a particular embodiment, the sequence tag is the same for each primer in the multiplexed amplification reaction. For example, in certain embodiments, the sequence tag is a 10-mer, such as -ACGTTGGATG- (SEQ ID NO: 1), and is attached to the 5' end of each primary and secondary primer. In particular embodiments of the methods provided herein, only a single primer pair is used to amplify each particular nucleic acid target-region.

In certain embodiments, methods described herein may be used to improve the detection the Y-chromosome in a maternal sample, which may be used to determine the sex of a fetus. The presence or absence of the Y-chromosome in a maternal sample may be determined by performing the SRY assay described in Example 3. The SRY assay is a highly sensitive quantitative internal standard assay that detects trace amounts of the Y-chromosome. In certain embodiments, other polymorphisms located on the Y-chromosome may be assayed according to the methods provided herein.

The presence or absence of the Y-chromosome in a maternal sample may also be determined by performing the AMG assay provided herein. The presence or absence of a target nucleic acid may be determined in combination with other assays, such as an RhD assay, blood type assay or sex test assay. The methods may also be used for other applications, including but not limited to, paternity testing, forensics or quality control assays.

In addition to prenatal applications, the methods find utility in a range of applications, including, but not limited to, detecting rare cancer mutations, detecting transplant rejection and forensics.

In certain embodiments, the total copy number of nucleic acid molecules for the human serum albumin (ALB) gene is determined. Methods for determining the total copy number of nucleic acid present in a sample comprise detecting albumin-specific extension products and comparing the relative amount of the extension products to competitors introduced to the sample. In a related embodiment, the invention in part provides compositions and methods to determine the relative amount of fetal DNA in a sample (e.g., when the sample is plasma from a pregnant woman carrying a male fetus), which comprises annealing one or more albumin gene sequences to the fetal DNA, the primers provided in FIG. 9; performing a primer extension reaction; and analyzing the primer extension products to determine the relative amount of ALB extension products, wherein maternal albumin nucleic acid has been reduced using the methods provided herein. In a related embodiment, the fetal ALB amplicon is first amplified using the amplification primers provided in FIG. 9. The assay is useful to measure how much nucleic acid (e.g., total copy number) is present in a sample or loaded into a particular reaction. The assay may serve as an internal control and a guide to the likelihood of success for a particular PCR reaction. For example, if only 400 copies of ALB are measured then the probability of detecting any fetal DNA may be considered low. In certain embodiments, the competitors provided in FIG. 9 are introduced as an internal standard to determine copy number. In one embodiment, 200, 300, 400, 500, 600, 700, 800 or more competitor molecules are introduced to the assay.

Methods described herein provide a number of advantageous. The methods allow a high sensitivity to detect polymorphic alleles (e.g., fetal identifiers) present at low relative percentages in a DNA mixture and present at low copy number. The methods may also be incorporated into multiplexed assays in a single reaction. The methods are readily implemented, and only add a single additional step to the many current detection methods.

Nucleases

Cleavage methods and procedures for selecting restriction enzymes for cutting nucleic acid at specific sites are well known to the skilled artisan. For example, many suppliers of restriction enzymes provide information on conditions and types of DNA sequences cut by specific restriction enzymes, including New England BioLabs, Pro-Mega Biochems, Boehringer-Mannheim, and the like.

The preparation of nucleic acid to be cleaved should be free of contaminants such as phenol, chloroform, alcohol, EDTA, detergents, or excessive salts, all of which can interfere with restriction enzyme activity.

Embodiments of the invention can be assembled from multiple restriction endonucleases (available from various vendors) that are chosen to correspond to appropriate polymorphic alleles, as long as the restriction endonuclease selects for one polymorphic allele over another and performs a digestion within the amplicon sequence such that it prevents a subsequent amplification event. In one embodiment, the amplicon is chosen such that it contains a variable nuclease restriction site and sequence identifier, which may or may not be the same as the restriction site. Also, the restriction enzyme need not cleave at the polymorphic site, for example, at the variable nucleotide of a SNP.

Restriction enzymes are traditionally classified into three types on the basis of subunit composition, cleavage position, sequence-specificity and cofactor-requirements. However, amino acid sequencing has uncovered extraordinary variety among restriction enzymes and revealed that at the molecular level there are many more than three different kinds.

Type I enzymes are complex, multisubunit, combination restriction-and-modification enzymes that cut DNA at random far from their recognition sequences. Originally thought to be rare, we now know from the analysis of sequenced genomes that they are common. Type I enzymes are of considerable biochemical interest but they have little practical value since they do not produce discrete restriction fragments or distinct gel-banding patterns.

Type II enzymes cut DNA at defined positions close to or within their recognition sequences. They produce discrete restriction fragments and distinct gel banding patterns, and they are the only class used in the laboratory for DNA analysis and gene cloning. Type II enzymes frequently differ so utterly in amino acid sequence from one another, and indeed from every other known protein, that they likely arose independently in the course of evolution rather than diverging from common ancestors.

The most common type II enzymes are those like HhaI, HindIII and NotI that cleave DNA within their recognition sequences. Enzymes of this kind are the principle ones available commercially. Most recognize DNA sequences that are symmetric because they bind to DNA as homodimers, but a few, (e.g., BbvCI: CCTCAGC) recognize asymmetric DNA sequences because they bind as heterodimers. Some enzymes recognize continuous sequences (e.g., EcoRI: GAATTC) in which the two half-sites of the recognition sequence are adjacent, while others recognize discontinuous sequences (e.g., BglI: GCCNNNNNGGC (SEQ ID NO: 2)) in which the half-sites are separated. Cleavage leaves a 3"-hydroxyl on one side of each cut and a 5"-phosphate on the other. They require only magnesium for activity and the corresponding modification enzymes require only S-adenosylmethionine. They tend to be small, with subunits in the 200-350 amino acid range.

The next most common type II enzymes, usually referred to as 'type IIs" are those like FokI and AlwI that cleave outside of their recognition sequence to one side. These enzymes are intermediate in size, 400-650 amino acids in length, and they recognize sequences that are continuous and asymmetric. They comprise two distinct domains, one for DNA binding, the other for DNA cleavage. They are thought to bind to DNA as monomers for the most part, but to cleave DNA cooperatively, through dimerization of the cleavage domains of adjacent enzyme molecules. For this reason, some type IIs enzymes are much more active on DNA molecules that contain multiple recognition sites. A wide variety of Type IIS restriction enzymes are known and such enzymes have been isolated from bacteria, phage, archeabacteria and viruses of eukaryotic algae and are commercially available (Promega, Madison Wis.; New England Biolabs, Beverly, Mass.). Examples of Type IIS restriction enzymes that may be used with the methods described herein include, but are not limited to enzymes such as those listed in Table IA.

TABLE 1A

| Enzyme-Source | Recognition/Cleavage Site | Supplier |
| --- | --- | --- |
| Alw I - *Acinetobacter lwoffii* | GGATC(4/5) | NE Biolabs |
| Alw26 I - *Acinetobacter lwoffi* | GTCTC(1/5) | Promega |
| Bbs I - *Bacillus laterosporus* | GAAGAC(2/6) | NE Biolabs |

TABLE 1A-continued

| Enzyme-Source | Recognition/Cleavage Site | Supplier |
|---|---|---|
| Bbv I - *Bacillus brevis* | GCAGC(8/12) | NE Biolabs |
| BceA I - *Bacillus cereus* 1315 | IACGGC(12/14) | NE Biolabs |
| Bmr I - *Bacillus megaterium* | CTGGG(5/4) | NE Biolabs |
| Bsa I - *Bacillus stearothermophilus* 6-55 | GGTCTC(1/5) | NE Biolabs |
| Bst71 I - *Bacillus stearothermophilus* 71 | GCAGC(8/12) | Promega |
| BsmA I - *Bacillus stearothermophilus* A664 | GTCTC(1/5) | NE Biolabs |
| BsmB I - *Bacillus stearothermophilus* B61 | CGTCTC(1/5) | NE Biolabs |
| BsmF I - *Bacillus stearothermophilus* F | GGGAC(10/14) | NE Biolabs |
| BspM I - *Bacillus* species M | ACCTGC(4/8) | NE Biolabs |
| Ear I - *Enterobacter aerogenes* | CTCTTC(1/4) | NE Biolabs |
| Fau I - *Flavobacterium aquatile* | CCCGC(4/6) | NE Biolabs |
| Fok I - *Flavobacterium okeonokoites* | GGATG(9/13) | NE Biolabs |
| Hga I - *Haemophilus gallinarum* | GACGC(5/10) | NE Biolabs |
| Ple I - *Pseudomonas lemoignei* | GAGTC(4/5) | NE Biolabs |
| Sap I - *Saccharopolyspora* species | GCTCTTC(1/4) | NE Biolabs |
| SfaN I - *Streptococcus faecalis* ND547 | GCATC(5/9) | NE Biolabs |
| Sth132 I - *Streptococcus thermophilus* ST132 | CCCG(4/8) | No commercial supplier (Gene 195: 201-206 (1997)) |

The third major kind of type II enzyme, more properly referred to as "type IV" are large, combination restriction-and-modification enzymes, 850-1250 amino acids in length, in which the two enzymatic activities reside in the same protein chain. These enzymes cleave outside of their recognition sequences; those that recognize continuous sequences (e.g., Eco57I: CTGAAG) cleave on just one side; those that recognize discontinuous sequences (e.g., BcgI: CGANNNNNNTGC (SEQ ID NO: 3)) cleave on both sides releasing a small fragment containing the recognition sequence. The amino acid sequences of these enzymes are varied but their organization are consistent. They comprise an N-terminal DNA-cleavage domain joined to a DNA-modification domain and one or two DNA sequence-specificity domains forming the C-terminus, or present as a separate subunit. When these enzymes bind to their substrates, they switch into either restriction mode to cleave the DNA, or modification mode to methylate it.

As discussed above, the length of restriction recognition sites varies. For example, the enzymes EcoRI, SacI and SstI each recognize a 6 base-pair (bp) sequence of DNA, whereas NotI recognizes a sequence 8 bp in length, and the recognition site for Sau3AI is only 4 bp in length. Length of the recognition sequence dictates how frequently the enzyme will cut in a random sequence of DNA. Enzymes with a 6 bp recognition site will cut, on average, every $4^6$ or 4096 bp; a 4 bp recognition site will occur roughly every 256 bp.

Different restriction enzymes can have the same recognition site—such enzymes are called isoschizomers. Table IB shows that the recognition sites for SacI and SstI are identical. In some cases isoschizomers cut identically within their recognition site, but sometimes they do not. Isoschizomers often have different optimum reaction conditions, stabilities and costs, which may influence the decision of which to use. Table IB is provided only to show exemplary restriction enzymes, and does not limit the scope of the invention in any way.

TABLE IB

| Enzyme | Recognition Sequence |
|---|---|
| BamH I | GGATCC<br>CCTAGG |
| Not I | GCGGCCGC<br>CGCCGGCG |
| Sau3A I | GATC<br>CTAG |
| Sac I | GAGCTC<br>CTCGAG |

TABLE IB-continued

| Enzyme | Recognition Sequence |
|---|---|
| Sst I | GAGCTC |
|  | CTCGAG |
| Hinf I | GANTC |
|  | CTNAG |
| Xho II | PuGATCPy |
|  | PyCTAGPu |

Restriction recognitions sites can be unambiguous or ambiguous. The enzyme BamHI recognizes the sequence GGATCC and no others; therefore it is considered "unambiguous." In contrast, HinfI recognizes a 5 bp sequence starting with GA, ending in TC, and having any base between (in Table IB, "N" stands for any nucleotide). HinfI has an ambiguous recognition site. XhoII also has an ambiguous recognition site: Py stands for pyrimidine (T or C) and Pu for purine (A or G), so XhoII will recognize and cut sequences of AGATCT, AGATCC, GGATCT and GGATCC.

The recognition site for one enzyme may contain the restriction site for another. For example, note that a BamHI recognition site contains the recognition site for Sau3AI. Consequently, all BamHI sites will cut with Sau3AI. Similarly, one of the four possible XhoII sites will also be a recognition site for BamHI and all four will cut with Sau3AI.

Also from Table IB, most recognition sequences are palindromes—they read the same forward (5' to 3' on the top strand) and backward (5' to 3' on the bottom strand). Most, but certainly not all recognition sites for commonly-used restriction enzymes are palindromes. Most restriction enzymes bind to their recognition site as dimers (pairs).

Nucleic Acid Detection

Whether detecting sequence differences, detecting amplification products or primer extension products, any detection or discrimination method known in the art may be utilized. These methods include, but are not limited to, primer extension reactions, mass spectrometry, hybridization using at least one probe, hybridization using at least one fluorescently labeled probe, direct sequencing, cloning and sequencing, and electrophoresis. Polymorphism detection methods known in the art may also include, for example, microsequencing methods, ligase sequence determination methods (e.g., U.S. Pat. Nos. 5,679,524 and 5,952,174, and WO 01/27326), digital PCR (U.S. Pat. No. 6,143,496), mismatch sequence determination methods (e.g., U.S. Pat. Nos. 5,851, 770; 5,958,692; 6,110,684; and 6,183,958), microarray sequence determination methods, restriction fragment length polymorphism (RFLP) procedures, PCR-based assays (e.g., TAQMAN®PCR System (Applied Biosystems)), nucleotide sequencing methods, hybridization methods, conventional dot blot analyses, single strand conformational polymorphism analysis (SSCP, e.g., U.S. Pat. Nos. 5,891,625 and 6,013,499; Orita et al., *Proc. Natl. Acad. Sci. U.S.A* 86: 27776-2770 (1989)), denaturing gradient gel electrophoresis (DGGE), heteroduplex analysis, mismatch cleavage detection, and techniques described in Sheffield et al., *Proc. Natl. Acad. Sci. USA* 49: 699-706 (1991), White et al., Genomics 12: 301-306 (1992), Grompe et al., *Proc. Natl. Acad. Sci. USA* 86: 5855-5892 (1989), and Grompe, *Nature Genetics* 5: 111-117 (1993), detection by mass spectrometry (e.g., US 20050079521, which is hereby incorporated by reference), real time-PCR (e.g., U.S. Pat. No. 5,210,015, U.S. Pat. No. 5,487,972, both of which are hereby incorporated by reference), or hybridization with a suitable nucleic acid primer specific for the sequence to be detected. Suitable nucleic acid primers can be provided in a format such as a gene chip.

Primer extension polymorphism detection methods, also referred to herein as "microsequencing" methods, typically are carried out by hybridizing a complementary oligonucleotide to a nucleic acid carrying the polymorphic site. In these methods, the oligonucleotide typically hybridizes adjacent to the polymorphic site. As used herein, the term "adjacent" refers to the 3' end of the extension oligonucleotide being sometimes 1 nucleotide from the 5' end of the polymorphic site, often 2 or 3, and at times 4, 5, 6, 7, 8, 9, or 10 nucleotides from the 5' end of the polymorphic site, in the nucleic acid when the extension oligonucleotide is hybridized to the nucleic acid. The extension oligonucleotide then is extended by one or more nucleotides, often 1, 2, or 3 nucleotides, and the number and/or type of nucleotides that are added to the extension oligonucleotide determine which polymorphic variant or variants are present. Oligonucleotide extension methods are disclosed, for example, in U.S. Pat. Nos. 4,656, 127; 4,851,331; 5,679,524; 5,834,189; 5,876,934; 5,908,755; 5,912,118; 5,976,802; 5,981,186; 6,004,744; 6,013,431; 6,017,702; 6,046,005; 6,087,095; 6,210,891; and WO 01/20039. The extension products can be detected in any manner, such as by fluorescence methods (see, e.g., Chen & Kwok, *Nucleic Acids Research* 25: 347-353 (1997) and Chen et al., *Proc. Natl. Acad. Sci. USA* 94/20: 10756-10761 (1997)) and by mass spectrometric methods (e.g., MALDI-TOF mass spectrometry). Oligonucleotide extension methods using mass spectrometry are described, for example, in U.S. Pat. Nos. 5,547,835; 5,605,798; 5,691,141; 5,849,542; 5,869,242; 5,928,906; 6,043,031; 6,194,144; and 6,258,538.

Microsequencing detection methods often incorporate an amplification process that proceeds the extension step. The amplification process typically amplifies a region from a nucleic acid sample that comprises the polymorphic site. Amplification can be carried out by utilizing a pair of oligonucleotide primers in a polymerase chain reaction (PCR), in which one oligonucleotide primer typically is complementary to a region 3' of the polymorphism and the other typically is complementary to a region 5' of the polymorphism. A PCR primer pair may be used in methods disclosed in U.S. Pat. Nos. 4,683,195; 4,683,202, 4,965,188; 5,656,493; 5,998,143; 6,140,054; WO 01/27327; and WO 01/27329 for example. PCR primer pairs may also be used in any commercially available machines that perform PCR, such as any of the GENEAMP® Systems available from Applied Biosystems.

A microarray can be utilized for determining whether a polymorphic variant is present or absent in a nucleic acid sample. A microarray may include any oligonucleotides described herein, and methods for making and using oligonucleotide microarrays suitable for prognostic use are disclosed in U.S. Pat. Nos. 5,492,806; 5,525,464; 5,589,330; 5,695,940; 5,849,483; 6,018,041; 6,045,996; 6,136,541; 6,142,681; 6,156,501; 6,197,506; 6,223,127; 6,225,625; 6,229,911; 6,239,273; WO 00/52625; WO 01/25485; and WO 01/29259. The microarray typically comprises a solid support and the oligonucleotides may be linked to this solid support by covalent bonds or by non-covalent interactions. The oligonucleotides may also be linked to the solid support directly or by a spacer molecule. A microarray may comprise one or more oligonucleotides complementary to a polymorphic site within a nucleotide sequence.

EXAMPLES

The following examples are provided to further describe embodiments of the invention and are not limiting.

Example 1

Restriction Endonuclease Enhanced Polymorphic Sequence Detection Using Hpych4v and NlaIII The effectiveness of restriction endonuclease enhanced polymorphic sequence detection was demonstrated using several restriction endonucleases (REs), including HpyCH4V and NlaIII (purchased from New England BioLabs, Inc). Both of these enzymes were separately tested in multiplexed genotyping reactions for their ability to specifically cleave one allele of a given polymorphism while allowing PCR amplification of the remaining allele of the polymorphism. See Table 2 for the polymorphisms tested with each enzyme.

Two CEPH DNA samples were mixed in varying ratios to generate DNA samples composed of 0%, 2%, 5%, 20%, 50% and 100% DNA heterozygous for both alleles of the SNP, with the remaining DNA being homozygous for the allele recognized by the RE. Table 3 shows DNA samples used in these studies and corresponding genotype information. Mixtures composed of NA05995 and NA10849 were used for experiments with HpyCH4V enzyme, and mixtures composed of NA10862 and NA10846 were used for experiments with NlaIII enzyme.

TABLE 2

Restriction enzymes recognizing SNPs

| Restriction Enzyme | Polymorphism | SNP Alleles | Allele Digested by RE |
|---|---|---|---|
|  | rs10430091 | A/T |  |
| NlaIII | rs2050927 | A/T | A |
| NlaIII, HpyCH4V | rs4329520 | A/T | T, T* |
|  | rs4657868 | A/T |  |
| HpyCH4V | rs4658481 | A/T | A |
|  | rs6693568 | A/T |  |
|  | rs860954 | A/T |  |
|  | rs9431593 | A/T |  |

*Both enzymes, NlaIII and HpyCH4V, digest the T allele.

TABLE 3

DNA samples used and genotypes

| | | SNP genotypes | | |
|---|---|---|---|---|
| Restriction Enzyme | DNA* | rs2050927 | rs4329520 | rs4658481 |
| HpyCH4V | NA05995 |  | TA | TA |
|  | NA10849 |  | T | A |
| NlaIII | NA10862 | AT | TA |  |
|  | NA10846 | A | T |  |

*DNA samples were obtained from Coriell CEPH DNA collection

TABLE 4

DNA mixtures (Listed as ng DNA per reaction)

| | | Relative percentage unrecognized SNP allele | | | | | |
|---|---|---|---|---|---|---|---|
| | | 0% | 2% | 5% | 20% | 50% | 100% |
| HpyCH4V | NA05995 | 0 | 0.6 | 0.6 | 0.6 | 0.6 | 0.6 |
|  | NA10849 | 0.6 | 29.4 | 11.4 | 2.4 | 0.6 | 0 |
| NlaIII | NA10862 | 0 | 0.6 | 0.6 | 0.6 | 0.6 | 0.6 |
|  | NA10846 | 0.6 | 29.4 | 11.4 | 2.4 | 0.6 | 0 |

NOTE:
Based on 3 pg DNA for haploid human genomic equivalent, 0.6 ng DNA is equal to 200 copies of genomic target DNA in the mixtures.

After preparation of the sample DNA mixtures, PCR cocktail was prepared according to Table 5 below (using multiplexed PCR primers as shown in Table 6) to either include no restriction endonuclease or 0.25 U of restriction endonuclease per each sample reaction. PCR cocktail was aliquoted to a 96-well plate to include 7 replicates of each DNA mixture for each enzyme condition. After addition of DNA to the PCR cocktail mixtures, samples were incubated at 37° C. for 1 hour to allow enzyme digestion of DNA samples and then immediately thermal cycled using standard conditions (Table 7).

TABLE 5

PCR cocktail preparation for each multiplex without DNA addition

| Reagents | Final Conc | No RE N = 1 (uL) | HpyCH4V N = 1 (uL) | NlaIII N = 1 (uL) |
|---|---|---|---|---|
| Water | n/a | 3 | 2.95 | 2.975 |
| 10xPCR Buffer (HotStar Taq Buffer) | 1.25x | 3.125 | 3.125 | 3.125 |
| $MgCl_2$ (25 mM) | 1.625 mM | 1.625 | 1.625 | 1.625 |
| PCR Nucleotide Mix (for UNG use) (10 mM dATP, dCTP, dGTP, dUTP) | 0.2 mM | 0.5 | 0.5 | 0.5 |
| F/R Primer mix (0.5 uM) | 0.1 μM | 5 | 5 | 5 |
| 5 U/ul HpyCH4V or 10 U/ul NlaIII | 0.25 U/rxn | — | 0.05 | 0.025 |
| 1 U/μl Uracil-DNA-Glycosylase (UDG) | 1.25 U/rxn | 1.25 | 1.25 | 1.25 |
| HotStar Taq (5 U/uL) | 2.5 U/rxn | 0.5 | 0.5 | 0.5 |
| DNA - added separately | varies | 10 | 10 | 10 |
| Total volume | n/a | 25 | 25 | 25 |

TABLE 6

PCR Primer sequences for SNPs

| SNP | Forward PCR Primer | SEQ ID NO: | Reverse PCR Primer | SEQ ID NO: |
|---|---|---|---|---|
| rs10430091 | ACGTTGGATGCACAAGATTCTGAAACTTAG | 4 | ACGTTGGATGGCTGTTTAACTCAGCATG | 12 |
| rs2050927 | ACGTTGGATGTTGGGTGCAGAGTAGTCATC | 5 | ACGTTGGATGTTCTAGCTTGCTTCTCCTCC | 13 |
| rs4329520 | ACGTTGGATGATGTCCACCTCCTGCTCCAC | 6 | ACGTTGGATGGAAAGTTGTCGTGGTAGAGG | 14 |
| rs4657868 | ACGTTGGATGCTAGCGTACCCAATGGAATC | 7 | ACGTTGGATGCTAACCAGGAAAAGACACCC | 15 |
| rs4658481 | ACGTTGGATGGTGGTAGAAACAAATGTCAGC | 8 | ACGTTGGATGCTGCTAAGCATGAGAGAAAG | 16 |
| rs6693568 | ACGTTGGATGGGCCTGTTCATTCTCAGAAA | 9 | ACGTTGGATGTGACTAGGAAATCACACTGG | 17 |
| rs860954 | ACGTTGGATGTAGCCTTTAGTCTTGATGCC | 10 | ACGTTGGATGCCATTCTTGTATGTTTTGTC | 18 |
| rs9431593 | ACGTTGGATGGCCTCAGTAGTCACATAAGG | 11 | ACGTTGGATGTTGAGATCAGTGTCGGTTCC | 19 |

Extend Primers

| SNP | Extend Primer | SEQ ID NO: |
|---|---|---|
| rs10430091 | gTGTTTAACTCAGCATGTGGGAA | 20 |
| rs2050927 | CCTCCATCATCCTTAGC | 21 |
| rs4329520 | GCGTGGTTCTAGACTTATGC | 22 |
| rs4657868 | cAAGACACCCCCATACATTA | 23 |
| rs4658481 | TAAGCATGAGAGAAAGGGAAAG | 24 |
| rs6693568 | atGAAATCACACTGGACATTTT | 25 |
| rs860954 | GTTTTGTCTTTTTCTGTATACTCATG | 26 |
| rs9431593 | TGTTCCTGACTCTCAAAAT | 27 |

TABLE 7

Thermal cycling conditions

| Temp. | Time | Cycles |
|---|---|---|
| 37° C. | 1 hour | 1 |
| 94° C. | 15 min | 1 |
| 94° C. | 20 sec | 45 cycles |
| 56° C. | 30 sec | |
| 72° C. | 1 min | |
| 72° C. | 3 min | 1 |
| 4° C. | forever | 1 |

Amplicon generated during PCR was genotyped with the extend primers in Table 5 using standard iPLEX™ assay and MassARRAY® technology (Jurinke, C., Oeth, P., van den Boom, D., MALDI-TOF mass spectrometry: a versatile tool for high-performance DNA analysis. *Mol. Biotechnol.* 26, 147-164 (2004); and Oeth, P. et al., iPLEX™ Assay: Increased Plexing Efficiency and Flexibility for MassARRAY® System through single base primer extension with mass-modified Terminators. SEQUENOM Application Note (2005), both of which are hereby incorporated by reference).

Results

Figure 2:
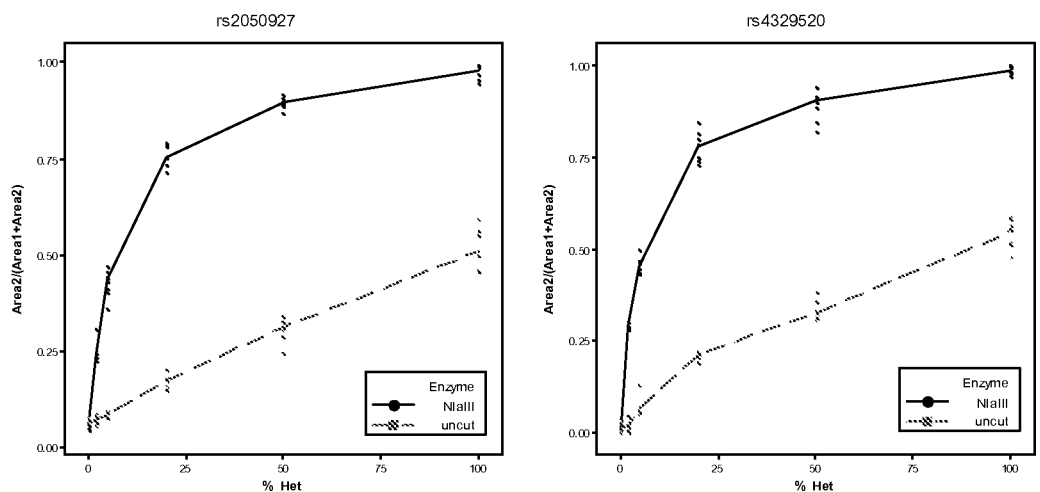
FIG. 2 is the NlaIII digest, which shows allele peak area ratios in a DNA mixture series. Peak area ratio is determined by dividing the calculated peak area of the SNP allele not recognized by NlaIII (i.e., target allele) by the total peak area of both SNP alleles present in the mass spectrum.
Figure 3:
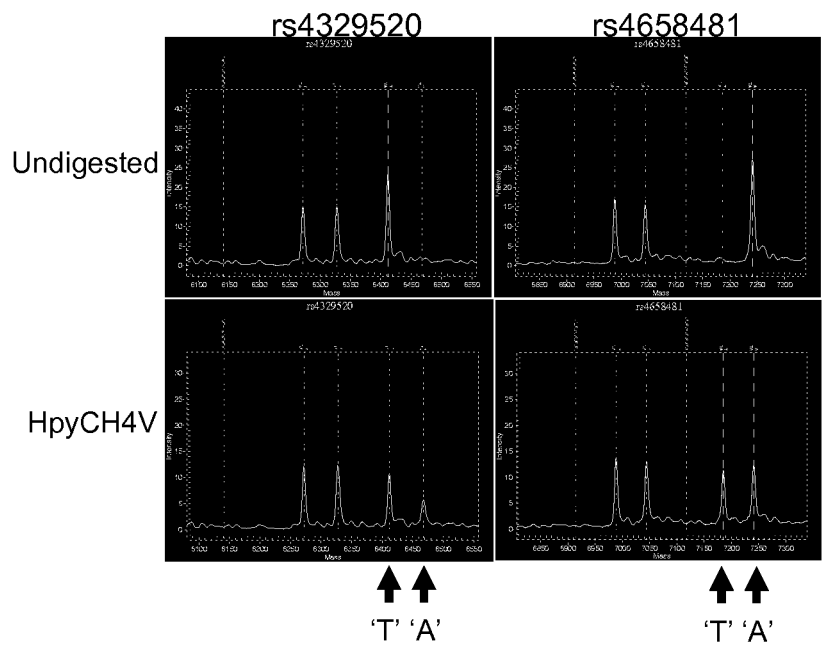
FIG. 3 is the HpyCH4V screenshots of 2% heterozygous DNA mixture. Note the appearance of the 'A' and 'T' alleles after HpyCH4V digestion of the DNA samples for rs4329520 and rs4658481, respectively.
Figure 4:
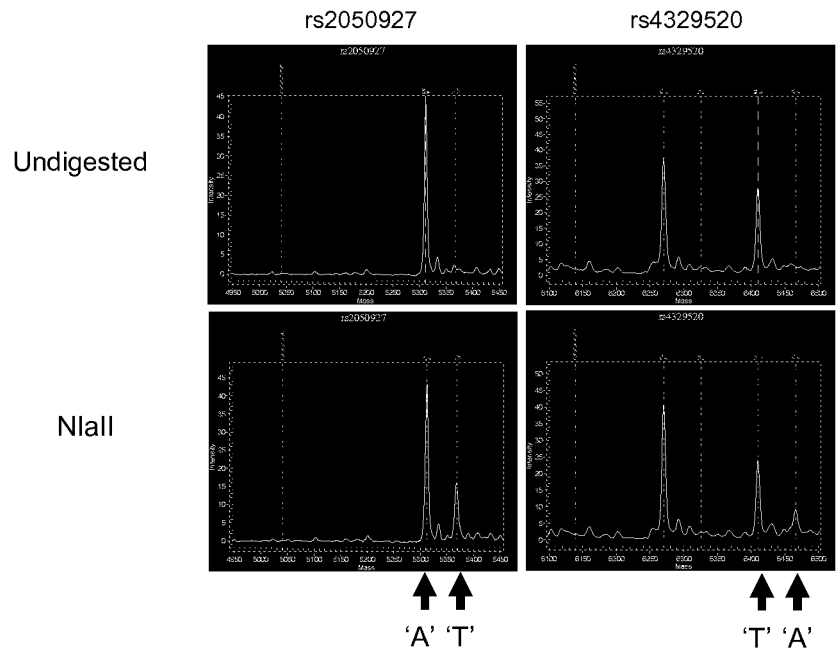
FIG. 4 is the NlaIII screenshots of 2% heterozygous DNA mixture. Note the appearance of the 'T' and 'A' alleles after NlaIII digestion of the DNA samples for rs2050927 and rs4329520, respectively.

Digestion of DNA with both restriction enzymes allowed detection of minor alleles when they were present at ratios as low as 2% heterozygous DNA. This is in contrast to undigested DNA samples where minor alleles were only reliably detected when present at ratios of 20% heterozygous DNA and higher. When allele peak area ratios are considered, the effect of restriction endonuclease digest is even more apparent. HpyCH4V digested samples showed minor allele peak area ratios of 0.35-0.45 in 2% heterozygous DNA mixtures, while minor allele peak area ratios of 2% heterozygous DNA mixtures were at background levels without enzyme digestion (FIG. 1). While the increases in allele peak area ratio were not as high when using the NlaIII restriction endonuclease, the results were similar (FIG. 2). Example screen shots of the mass spectrum in 2% heterozygous DNA mixtures with and without HpyCH$_4$V (FIG. 3) or NlaIII (FIG. 4) are shown below.

Optimization Studies

Initial optimization studies for enzyme concentration and pre-PCR incubation time of HpyCH$_4$V digestion were performed using 5% heterozygous DNA mixtures (0.6 ng heterozygous DNA, 11.4 ng homozygous DNA). Based on these experiments, maximal peak area ratios were obtained with incubation times as short as 5 minutes and 0.25 U HpyCH$_4$V enzyme.

Example 2

Restriction Endonuclease Enhanced Polymorphic Sequence Detection Using Tfii

A similar experiment was performed as described in Example 1 using a different restriction endonuclease, TfiI. In this experiment, the TfiI restriction endonuclease selectively recognized and cleaved the 'C' allele of the 'C/T' SNP, rs4487973. The SNP rs4487973 occurs in the following genomic sequence on chromosome 1: CACACAGTTAG-GATT[C/T]ACCTGAGCTTGTCCC (SEQ ID NO: 28). For these studies, two CEPH DNA samples, one homozygous 'C' and the other heterozygous 'C/T' for the rs4487973 SNP, were mixed in varying ratios to generate DNA mixtures containing 0%, 1%, 2.5%, 10%, 50% of the rs4487973 'T' allele. The TfiI restriction endonuclease was either added or not added to each mixture to determine the endonucleases' effect on detecting the polymorphic sequence. Of the mixtures not digested with TfiI enzyme, the rs4487973 'T' allele was detected in the 10%, and 50% 'T' allele mixtures, but not the 0%, 1%, and 5% 'T' allele DNA mixtures. However, of samples digested with TfiI enzyme, the rs4487973 'T' allele was detectable in 1%, 5%, 10% and 50% 'T' allele mixtures. These results indicate the utility of this method to improve detection of polymorphic alleles present at low relative concentrations in a sample.

Example 3

Fetal Identifiers, Sex Test And Copy Number Determination

Selection of SNPs

Analysis of paternally-inherited alleles in clinical samples and correlation with Y-chromosome frequency in male fetuses was performed with a total of 16 SNPs. SNP assays for analysis of clinical samples were multiplexed as 8-plexes. All SNPs had a minor allele frequency (maf) of ~0.4 in all ethnic groups and were unlinked.

For performance evaluation of a universal Fetal Identifier panel that can be multiplexed with disease-specific markers, a new panel of 87 NT SNPs with a pan-ethnic maf >0.4 was selected and multiplexed into 16-plexes.

Method of SNP Analysis

Figure 5A:
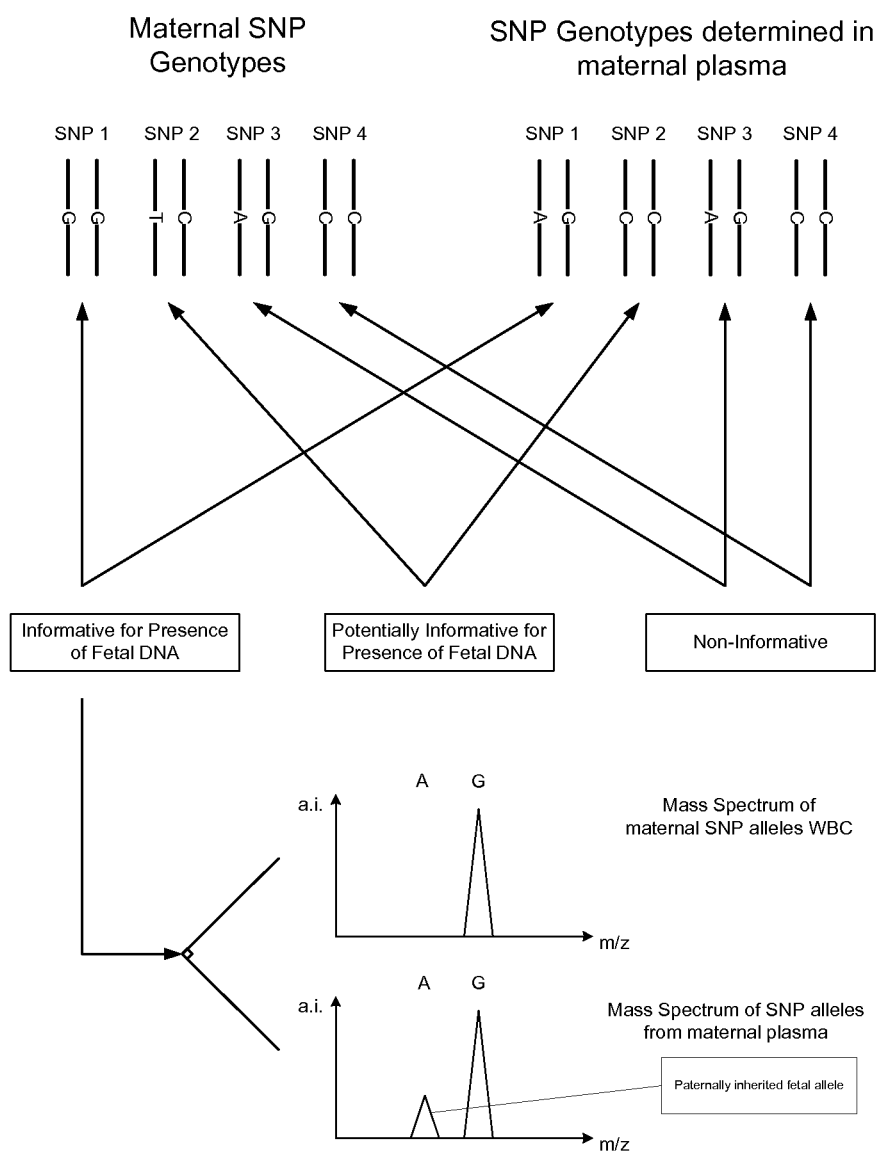
FIG. 5A shows the use of single nucleotide polymorphisms (SNP's) Fetal Identifiers to confirm the presence of fetal DNA by paternally-inherited alleles.
Figure 5B:
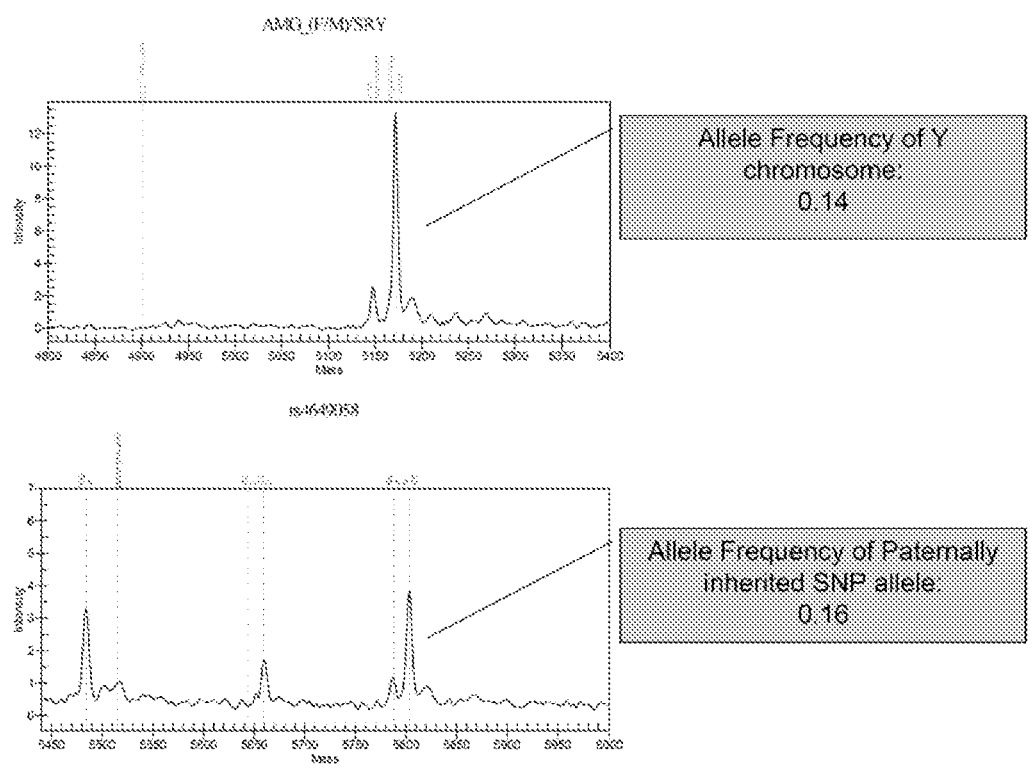
FIG. 5B shows representative mass spectra demonstrating the correlation between fetal DNA amounts estimated from AMG XY and from Fetal Identifier assays. The results were generated using the AMG primers provided in FIG. 9.

Analysis of SNPs in maternal buffy coat and maternal plasma was performed using the iPLEX™ assay and MassARRAY® technology. In brief, the target region surrounding the SNP is first amplified by PCR. Subsequently an oligonucleotide primer is annealed to the PCR product and is extended allele-specifically by a single nucleotide using a mixture of 4 terminator nucleotides and a DNA polymerase. The extension products are transferred to a miniaturized chip array and are analyzed by MALDI-TOF Mass Spectrometry. Determination of the molecular mass of extension products allows unambiguous identification of the SNP allele present in the sample. The peak area ratio of mass signals allows the estimation of the relative abundance of the alleles in a given sample. FIG. 5A provides an overview of the assay used for SNP analysis.

Clinical Samples

The total sample set consisted of 35 paired blood/plasma samples from pregnant Caucasian woman (nine 1st trimester; twelve 2nd trimester; fourteen 3rd trimester).

The subset of samples used for correlation of Y-chromosome frequency and paternally-inherited alleles in maternal plasma consisted of 19 samples of pregnant Caucasian woman carrying a male fetus.

DNA Extraction

DNA extraction was performed from 1 ml of maternal plasma using the Qiagen® MinElute kit for fetal genotyping.

DNA extraction from frozen blood (minus plasma) was performed from 4 ml using Qiagen's PureGene kit for maternal genotyping.

Results

An assay targeting sequence differences in the Amelogenin region on the X and Y chromosome was used to assess the relative amount of fetal DNA extracted from plasma of pregnant woman carrying a male fetus. Details of the AMG assay are depicted in FIGS. 8A-8C. X and Y-specific sequences can be discriminated by sequence specific iPLEX extension products and their respective mass signals. The peak area ratio of the extension products allows estimation of the relative amount of fetal DNA, because the Y-specific sequences represent 50% of the total fetal DNA contribution.

Sixteen of nineteen (84%) plasma samples with a male fetus showed a Y-chromosome frequency of higher than 5%, indicating presence of at least 10% fetal DNA in the extracted DNA.

Figure 6:
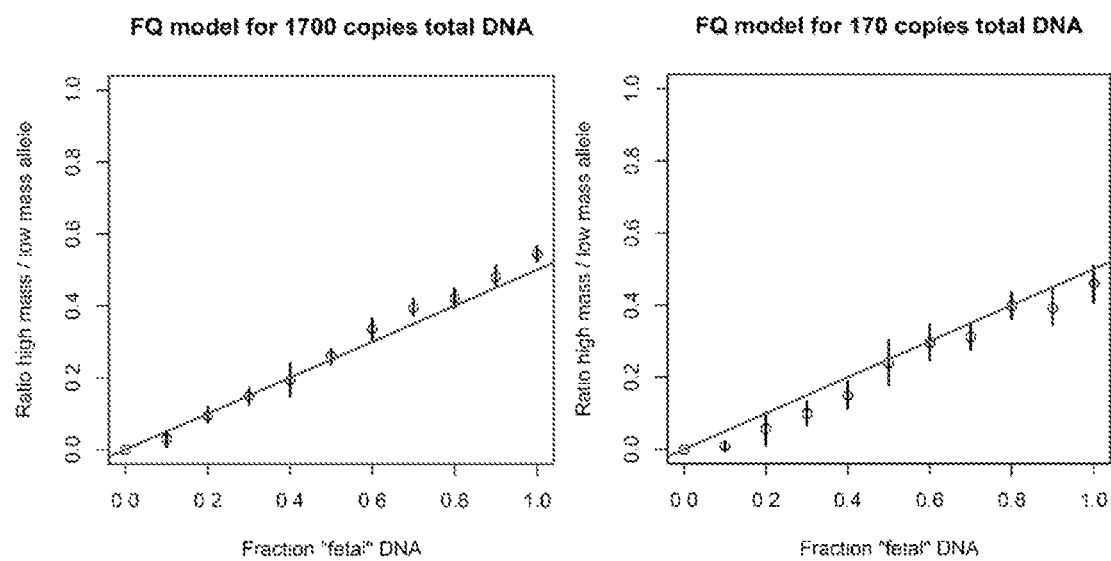
FIG. 6 depicts typical performance results for a qualified fetal identifier. Here the ability of the SNP assay to estimate the quantity of fetal DNA in the background of maternal DNA was verified for a total of 1700 copies and a total of 170 copies using genomic DNA mixtures. Note that the standard deviation of the estimate of fetal DNA increases due to the significant influence of the sampling error at low copy numbers.

FIG. 6 depicts typical performance results for a qualified fetal identifier. Here the ability of the SNP assay to estimate the quantity of fetal DNA in the background of maternal DNA was verified for a total of 1700 copies and a total of 170 copies using genomic DNA mixtures. Note that the standard deviation of the estimate of fetal DNA increases due to the significant influence of the sampling error at low copy numbers Table 8 provides a list of SNPs that were multiplexed at 10+ plexing level and passed all phases of the validation. The following shows the validation scheme, performance criteria and model system used to qualify multiplex SNP assays for their utility in identifying the presence for fetal DNA:

Phase I
   Step 1: Initial Fetal Identifier (FI) screening parameters
      FI's are multiplexed from pool of 87 A/T SNPs (mass difference 56 Da)
      Genotyping of control DNAs (CEPH populations)
   Step 2: Advance screening criteria
      Reproducibility of genotyping calls in 4 replicates
      Unambiguous genotype data (assay shows no interfering or unpredicted mass signals)
      Allelic skew in heterozygous DNAs
      Variance of allelic ratio in heterozygous DNAs
   Step 3: Replex successful SNPs and repeat Phase 1 screening to generate multiplexes of 10+ SNPs
Multiplexed SNPs passing Phase I test criteria are tested in Phase II
Phase II
   Step 1: Mixtures of Genomic DNA are used for assessing FI reliability
      Mix Mother: 2000 copies of DNA1
      Mix 10%: 3600 copies DNA 1/400 copies of DNA 2
      Mix 20%: 1600 copies DNA 1/400 copies of DNA 2
   Analysis of allele frequency variation in 4 mixture series and 8 replicate measurements. Sensitivity and specificity are calculated for the detection of low copy number allele in background of high copy number allele Multiplexed SNPs passing Phase II test criteria are tested in Phase III Phase III Step 1: Various DNAs are mixed to emulate different maternal-fetal combinations
  Plate 1: 3600 copies DNA maternal/400 copies DNA fetal
  Plate 2: 1600 copies DNA maternal/400 copies DNA fetal
    Each plate contains 88 sample mixtures, 4 positive and 4 negative controls. Analysis of allele frequency variation in 4 mixture series, where sensitivity and specificity are calculated for the detection of low copy number allele in background of high copy number allele Application of this assay panel to a model system for the detection of fetal DNA in maternal background showed that paternally-inherited fetal alleles can be detected with a sensitivity of 95% at 100% specificity if the sample preparation method can enrich the relative amount of fetal DNA to 20%. In Table 8, the minor allele frequency (MAF) for each SNP from different ethnic populations is provided. The ethnic populations are defined by the HapMap Project, where CEU represents individuals of Northern and Western Europe descent, HCB represents Han Chinese in Beijing, JAP represents Japanese in Tokyo, and YRI represents the Yoruba in Ibadan, Nigeria.

TABLE 8

| SNP | MAF CEU | MAF HCB | MAF JAP | MAF YRI |
| --- | --- | --- | --- | --- |
| rs11166512 | 0.43 | 0.41 | 0.50 | 0.49 |
| rs11184494 | 0.50 | 0.40 | 0.48 | 0.50 |
| rs11247894 | 0.43 | 0.39 | 0.32 | 0.44 |
| rs12089156 | 0.46 | 0.49 | 0.44 | 0.43 |

TABLE 8-continued

| SNP | MAF CEU | MAF HCB | MAF JAP | MAF YRI |
| --- | --- | --- | --- | --- |
| rs12125888 | 0.40 | 0.43 | 0.48 | 0.43 |
| rs12136370 | 0.42 | 0.48 | 0.42 | 0.48 |
| rs12143315 | 0.40 | 0.42 | 0.42 | 0.42 |
| rs12759642 | 0.39 | 0.48 | 0.48 | 0.42 |
| rs156988 | 0.46 | 0.40 | 0.45 | 0.41 |
| rs2050927 | 0.44 | 0.50 | 0.41 | 0.49 |
| rs213624 | 0.48 | 0.44 | 0.40 | 0.34 |
| rs2454175 | 0.46 | 0.48 | 0.43 | 0.40 |
| rs4329520 | 0.45 | 0.43 | 0.40 | 0.44 |
| rs4487973 | 0.47 | 0.43 | 0.44 | 0.40 |
| rs454782 | 0.48 | 0.40 | 0.41 | 0.46 |
| rs4648888 | 0.33 | 0.30 | 0.33 | 0.46 |
| rs635364 | 0.49 | 0.40 | 0.46 | 0.43 |
| rs660279 | 0.41 | 0.49 | 0.50 | 0.39 |
| rs6687785 | 0.48 | 0.46 | 0.48 | 0.44 |
| rs7551188 | 0.46 | 0.49 | 0.45 | 0.46 |
| rs9431593 | 0.41 | 0.43 | 0.49 | 0.40 |

A multiplexed panel of 16 SNPs was analyzed with maf>0.3 in the same maternal plasma DNA extraction and established a baseline of maternal genotypes by analyzing DNA from PBMCs. Using the maternal genotype information, paternally-inherited alleles were identified in plasma samples and estimated the amount of fetal DNA from the peak area ratio of extension products representing paternally-inherited fetal alleles and maternal alleles.

Figure 7:
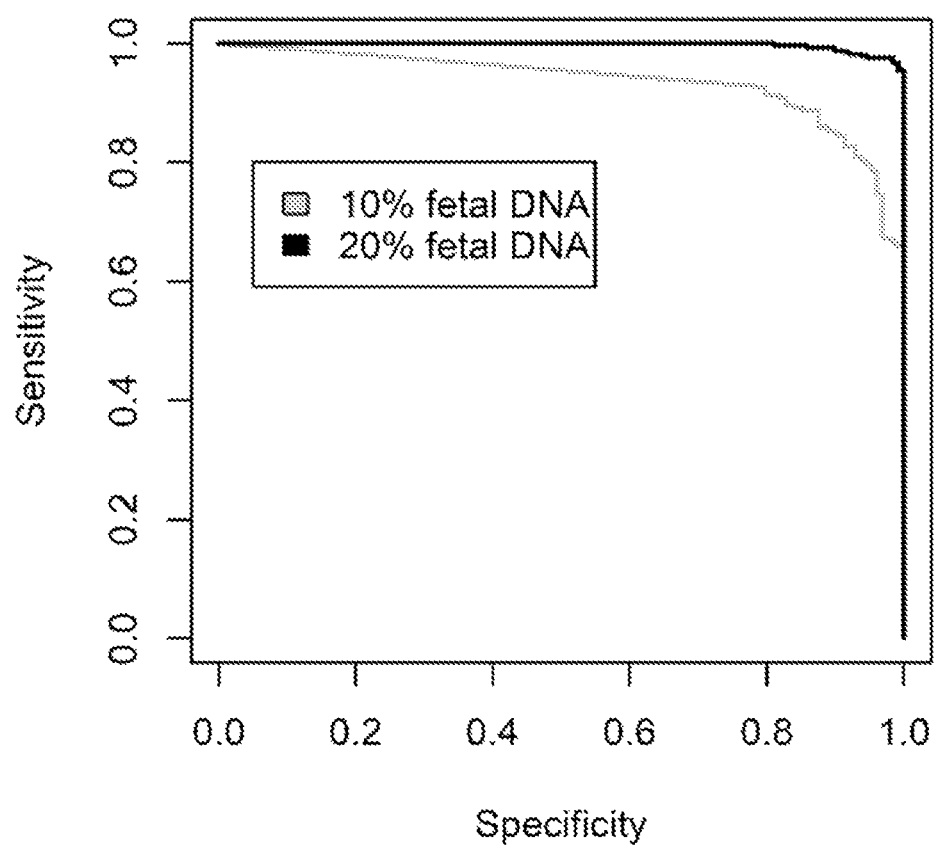
FIG. 7 shows the performance of multiplexed SNP assays (21 assays total) for detection of paternally-inherited alleles in a model system.

The AMG XY frequency was then compared with the allele-frequency of paternally-inherited fetal alleles in informative SNPs. This comparison revealed that samples with a positive Y-frequency of 10% (used as a Limit-of-quantitation threshold) or more have significantly higher differences between maternally and paternally-inherited fetal allele-frequencies (p-value <0.001; Fishers' exact test). This data suggests that Fetal Identifiers can be used as a non-gender specific approach for identification of the presence of fetal DNA. FIG. 7 exemplifies those results.

TABLE 9

| Multiplex | Primer Name | Amplification primer | SEQ ID NO: | Amplification primer | SEQ ID NO: | Extend Primer sequence | SEQ ID NO: |
| --- | --- | --- | --- | --- | --- | --- | --- |
| MP1 | rs7551188 | ACGTTGGATGATCCCTGGTTCCTTCCTTAG | 29 | ACGTTGGATGGAGCCTCTCAGTGTCTATAC | 51 | GGACAGATTCTGGGAC | 73 |
| MP1 | rs11247894 | ACGTTGGATGATCCTAGATAGCCCAAAGCC | 30 | ACGTTGGATGGGAGGAAAGAGAAGATTGTG | 52 | CCAAAGCCAAGAATTCA | 74 |
| MP1 | rs6687785 | ACGTTGGATGATGCTGTAAAGAGCCTCAAC | 31 | ACGTTGGATGTTCTCCTCTGACCTGCTTTC | 53 | CCTCAACAGTACACTTAATC | 75 |
| MP1 | rs4487973 | ACGTTGGATGTCAGAGAGTGACAAGACCTG | 32 | ACGTTGGATGGAATGCATGCCAACTTAGGG | 54 | cAGGTCACACAGTTAGGATT | 76 |
| MP1 | rs4648888 | ACGTTGGATGCAGAGAGTCCCCTGTTATTG | 33 | ACGTTGGATGTGCCCAGACCAGAGAGGTCA | 55 | aTGGACCTTCGGAAAGGATA | 77 |
| MP1 | rs12089156 | ACGTTGGATGGCTACATACTATGTGGTCTC | 34 | ACGTTGGATGCCTGCTGGCAACAAATCTTC | 56 | TACTATGTGGTCTCAACTATAT | 78 |
| MP1 | rs2050927 | ACGTTGGATGTTCTAGCTTGCTTCTCCTCC | 35 | ACGTTGGATGTTGGGTGCAGAGTAGTCATC | 57 | TGCTTCTCCTCCATCATCCTTAGC | 79 |
| MP1 | rs12125888 | ACGTTGGATGCAACATCCTGTACATCACTC | 36 | ACGTTGGATGAGACAATTTCTGTCCTCTGG | 58 | TACATGACTATCTCCTCCCTTAGGT | 80 |
| MP1 | rs12143315 | ACGTTGGATGACAGGCATGAGCCATCTTAC | 37 | ACGTTGGATGTGCCATTGGTACAGTCACTC | 59 | CCATCTTACCCAGCCTCTTTCTTCAA | 81 |
| MP1 | rs213624 | ACGTTGGATGTAGGTCAAGCCAAGGCCTC | 38 | ACGTTGGATGTGTCCACCCAGGAGCAGCCA | 60 | gGCCAAGGCCTCGGAGTCTGAACAGTT | 82 |

TABLE 9-continued

| Multi-plex | Primer Name | Amplification primer | SEQ ID NO: | Amplification primer | SEQ ID NO: | Extend Primer sequence | SEQ ID NO: |
|---|---|---|---|---|---|---|---|
| MP1 | SRY_5-ib | ACGTTGGATGAGCATCTAGGTAGGTCTTTG | 39 | ACGTTGGATGAGCAACGGGACCGCTACAG | 61 | cGTTACCCGATTGTCCTAC | 83 |
| MP2 | rs660279 | ACGTTGGATGTTTCAGCAACCACTCTGAGC | 40 | ACGTTGGATGTGCCCGTAAGTAGGAGAGTG | 62 | CTTGATGTGCTTCCCTG | 84 |
| MP2 | rs635364 | ACGTTGGATGGAAATTTCTGGATTACTGGC | 41 | ACGTTGGATGAGAGACTCCATTTGTTTGGG | 63 | TGGATTACTGGCAAAGAC | 85 |
| MP2 | rs9431593 | ACGTTGGATGTTGAGATCAGTGTCGGTTCC | 42 | ACGTTGGATGGCCTCAGTAGTCACATAAGG | 64 | TGTTCCTGACTCTCAAAAT | 86 |
| MP2 | rs11166512 | ACGTTGGATGCTTCATCCACTATATCCACC | 43 | ACGTTGGATGTGACCAGATGTTGGATTAG | 65 | CCACTATATCCACCTTTTCT | 87 |
| MP2 | rs4329520 | ACGTTGGATGGAAAGTTGTCGTGGTAGAGG | 44 | ACGTTGGATGATGTCCACCTCCTGCTCCAC | 66 | GCGTGGTTCTAGACTTATGC | 88 |
| MP2 | rs454782 | ACGTTGGATGCTGTTAAGATGCCAACTCCC | 45 | ACGTTGGATGCTGTCTTCCTCATTGCTCTG | 67 | AACTCCCATATTAGTCCACAG | 89 |
| MP2 | rs12136370 | ACGTTGGATGGAGTAGTTCTTTGCAGTAAGC | 46 | ACGTTGGATGCTCCTGGAAAACAGCAAAAG | 68 | gGCAGTAAGCTATTCTTGGGG | 90 |
| MP2 | rs12759642 | ACGTTGGATGATTCTTCCTGGGACTCAGAC | 47 | ACGTTGGATGGGAAATACCAGCAACCACAG | 69 | caTCGGGATTCCCTGAACAAA | 91 |
| MP2 | rs11184494 | ACGTTGGATGAGCTGGCCATGTTTATTTGAC | 48 | ACGTTGGATGGCCAATCTATGAAGAATTAC | 70 | ATTTGACTTTCCTACTCCTTAAC | 92 |
| MP2 | rs2454175 | ACGTTGGATGGGAATCAGACCTGTAAACAC | 49 | ACGTTGGATGGCCCAGCAGGACACTTTTAT | 71 | cCTTCAAGGATTGGAATTAGAGT | 93 |
| MP2 | rs156988 | ACGTTGGATGAAAGCTCTGTGATGCGTCTC | 50 | ACGTTGGATGGAAAGGGCTATGTAAGGAGG | 72 | tCGTCTCGGTCCTTCCTTTTCACTT | 94 |

TABLE 10

| Multi-plex | SNP_ID | Amplification primer | SEQ ID NO: | Amplification primer | SEQ ID NO: | Extend Primer sequence | SEQ ID NO: |
|---|---|---|---|---|---|---|---|
| W1 | rs10793675 | ACGTTGGATGAAGAGATGAGACAGACTGGG | 95 | ACGTTGGATGCTCTGTATTTATAGCTTTC | 134 | AACGGCTCAACAGTT | 173 |
| W1 | rs1829309 | ACGTTGGATGATCTCTGAGTTGACACCACC | 96 | ACGTTGGATGTTCCTAATCAGGAGAGACCG | 135 | TTGCTTTGGGGAGCAG | 174 |
| W1 | rs660279 | ACGTTGGATGTTTCAGCAACCACTCTGAGC | 97 | ACGTTGGATGTGCCCGTAAGTAGGAGAGTG | 136 | CTTGATGTGCTTCCCTG | 175 |
| W1 | rs635364 | ACGTTGGATGGAAATTTCTGGATTACTGGC | 98 | ACGTTGGATGAGAGACTCCATTTGTTTGGG | 137 | TGGATTACTGGCAAAGAC | 176 |
| W1 | rs9431593 | ACGTTGGATGTTGAGATCAGTGTCGGTTCC | 99 | ACGTTGGATGGCCTCAGTAGTCACATAAGG | 138 | TGTTCCTGACTCTCAAAAT | 177 |
| W1 | rs11166512 | ACGTTGGATGCTTCATCCACTATATCCACC | 100 | ACGTTGGATGTGACCAGATGTTGGATTAG | 139 | CCACTATATCCACCTTTTCT | 178 |
| W1 | rs4329520 | ACGTTGGATGGAAAGTTGTCGTGGTAGAGG | 101 | ACGTTGGATGATGTCCACCTCCTGCTCCAC | 140 | GCGTGGTTCTAGACTTATGC | 179 |
| W1 | rs454782 | ACGTTGGATGCTGTTAAGATGCCAACTCCC | 102 | ACGTTGGATGCTGTCTTCCTCATTGCTCTG | 141 | AACTCCCATATTAGTCCACAG | 180 |
| W1 | rs12136370 | ACGTTGGATGGAGTAGTTCTTTGCAGTAAGC | 103 | ACGTTGGATGCTCCTGGAAAACAGCAAAAG | 142 | gGCAGTAAGCTATTCTTGGGG | 181 |
| W1 | rs12759642 | ACGTTGGATGATTCTTCCTGGGACTCAGAC | 104 | ACGTTGGATGGGAAATACCAGCAACCACAG | 143 | caTCGGGATTCCCTGAACAAA | 182 |

TABLE 10-continued

| Multi-plex | SNP_ID | Amplification primer | SEQ ID NO: | Amplification primer | SEQ ID NO: | Extend Primer sequence | SEQ ID NO: |
|---|---|---|---|---|---|---|---|
| W1 | rs11184494 | ACGTTGGATGAGCTGGCCATGTTTATTTGAC | 105 | ACGTTGGATGGCCAATCTATGAAGAATTAC | 144 | ATTTGACTTTCCTACTCCTTAAC | 183 |
| W1 | rs2454175 | ACGTTGGATGGGAATCAGACCTGTAAACAC | 106 | ACGTTGGATGGCCCAGCAGGACACTTTTAT | 145 | cCTTCAAGGATTGGAATTAGAGT | 184 |
| W1 | rs1452628 | ACGTTGGATGGCTTGTGCTTTGTTGTGTGG | 107 | ACGTTGGATGGGTCAAGCAAGGCTTCAAG | 146 | acatAGTTATTCCTAGGGCTTCTC | 185 |
| W1 | rs156988 | ACGTTGGATGAAAGCTCTGTGATGCGTCTC | 108 | ACGTTGGATGGAAAGGGCTATGTAAGGAGG | 147 | tCGTCTCGGTCCTTCCTTTTCACTT | 186 |
| W1 | rs4570430 | ACGTTGGATGACCCGAGCCAATCAGGTATC | 109 | ACGTTGGATGGCACATGGAGATGAATGGTC | 148 | GGTATCATAAGATACCTATGATGTC | 187 |
| W1 | rs12062414 | ACGTTGGATGTGCGTCAACCTTTCCAGTTC | 110 | ACGTTGGATGGGAAAGTCCTCGACTGTTTG | 149 | ggaaTTTCCAGTTCTATTCCAGCCTC | 188 |
| W1 | rs7545381 | ACGTTGGATGCCAGTCAAGCTAAGGACAAA | 111 | ACGTTGGATGGTGAGCACAACTGTGTTCTA | 150 | tccCTGAATGACAAAGGGGAAGATA | 189 |
| W1 | rs6427673 | ACGTTGGATGGGACTAAAACAGGGCCAAAC | 112 | ACGTTGGATGGTCTCTCTAGTACTAGTAAC | 151 | ccctcGCCAAACTTAGACCAAGGACAAC | 190 |
| W1 | rs10802761 | ACGTTGGATGTCTTCTAAAATGTAGTTATG | 113 | ACGTTGGATGGGATGAGGTTTTGACTAAGC | 152 | AGTTATGAAATAAGTTTTATTCATTTAC | 191 |
| W2 | rs642449 | ACGTTGGATGCCAAAAACCATGCCCTCTG | 114 | ACGTTGGATGAGATTGCCTCTCCATGTGAC | 153 | CCTCTGCCTCCCCTA | 192 |
| W2 | rs4839419 | ACGTTGGATGCTGCCGCATCCCTTCACAA | 115 | ACGTTGGATGATGTGTTTGTGGCCACTTCC | 154 | CCTTCACAAAGCCGA | 193 |
| W2 | rs9324198 | ACGTTGGATGAAAGGCCTACTGTTTGCTGG | 116 | ACGTTGGATGCAAAATATGTGAATCAGC | 155 | cGTTTGCTGGAAGCCT | 194 |
| W2 | rs1192619 | ACGTTGGATGGCTCAACTCTGAACCAATCG | 117 | ACGTTGGATGCCAGGAATGGGCATGTGTTC | 156 | TGGCCAGAAGAAGGAG | 195 |
| W2 | rs4657868 | ACGTTGGATGCTAACCAGGAAAAGACACCC | 118 | ACGTTGGATGCTAGCGTACCCAATGGAATC | 157 | AGACACCCCATACATTA | 196 |
| W2 | rs6426873 | ACGTTGGATGTAAATCAGGGCTGCCTTCTC | 119 | ACGTTGGATGAAGTGCTAGGGTTACAGGTG | 158 | cccCTGCCTTCTCTTCCAA | 197 |
| W2 | rs438981 | ACGTTGGATGTGTGCAAATTGGCTAACAT | 120 | ACGTTGGATGGAACATTGGTATTTAAACTC | 159 | ATGGACCACAAAAAACTTA | 198 |
| W2 | rs12125888 | ACGTTGGATGAGACAATTTCTGTCCTCTGG | 121 | ACGTTGGATGCAACATCCTGTACATCACTC | 160 | TCTGTCCTCTGGTATCCTCT | 199 |
| W2 | rs3128688 | ACGTTGGATGATCAAGAGGAAAATGGACAG | 122 | ACGTTGGATGGATTTACTCAACTCTCTGGG | 161 | cAAAATGGACAGAAGTTGAA | 200 |
| W2 | rs4987351 | ACGTTGGATGGTGCATGGGCTCATCTAGAC | 123 | ACGTTGGATGCCAAACAGGGCCAATGGTAG | 162 | gCATCTAGACACATTTTGTGC | 201 |
| W2 | rs6692911 | ACGTTGGATGCTATTCCCTCCTCAAAGAGC | 124 | ACGTTGGATGATTAAGATGGGTAGTTAAG | 163 | tccAAGAGCATTTTCCTCTTC | 202 |
| W2 | rs6684679 | ACGTTGGATGTATGTTACTTGCCTTGGCCC | 125 | ACGTTGGATGTCTTAAGGTGTCTCCCTCTG | 164 | ggaCCACTGAGGAGATACACTA | 203 |
| W2 | rs4320829 | ACGTTGGATGGGTTCTATGGCTTTGGTGAG | 126 | ACGTTGGATGTGCTAGACACTTTAACTGCC | 165 | ggtcACCTCTTTTCATAACAGGA | 204 |
| W2 | rs4658481 | ACGTTGGATGCTGCTAAGCATGAGAGAAAG | 127 | ACGTTGGATGGTGGTAGAAACAAATGTCAGC | 166 | atacGCATGAGAGAAAGGGAAAG | 205 |
| W2 | rs3768458 | ACGTTGGATGCCAAATGTCTTAGTTACAAAG | 128 | ACGTTGGATGGAGTTTATGTAATGTCAAC | 167 | CTTAGTTACAAAGAAAATTGTGAG | 206 |
| W2 | rs860954 | ACGTTGGATGTAGCCTTTAGTCTTGATGCC | 129 | ACGTTGGATGCCATTCTTGTATGTTTTGTC | 168 | TCTTGATGCCTTACAAAATAAATAT | 207 |

TABLE 10-continued

| Multi-plex | SNP_ID | Amplification primer | SEQ ID NO: | Amplification primer | SEQ ID NO: | Extend Primer sequence | SEQ ID NO: |
|---|---|---|---|---|---|---|---|
| W2 | rs10453878 | ACGTTGGATGGAGGAGCTAACAAGTAGGAC | 130 | ACGTTGGATGGGGATATGAATTACAACAGAG | 169 | AAACAAATCCTCCTTTCTTTTAATTC | 208 |
| W2 | rs10753912 | ACGTTGGATGGAGATTATATGTCTCTTTAA | 131 | ACGTTGGATGATTCTTCTAACTTTTAGGC | 170 | GAGATTATATGTCTCTTTAATATTGTC | 209 |
| W2 | rs1637944 | ACGTTGGATGCTAATGCCTCCTTTTCTTCC | 132 | ACGTTGGATGAATAGCAAACAACAGGTGGG | 171 | cccccATATCATTTGCAATTGCATGGTT | 210 |
| W2 | rs4839282 | ACGTTGGATGGAATCCTGGCAGCTCATTAG | 133 | ACGTTGGATGTGGGTTCACATGAGTCTTGC | 172 | gatgTCTCTTAAAGAGCAAAAAGCTAAG | 211 |

TABLE 11

| SNP ID | Amplification primer | SEQ ID NO: | Amplification primer | SEQ ID NO: | Extend Primer sequence | SEQ ID NO: |
|---|---|---|---|---|---|---|
| rs4292357 | ACGTTGGATGCTTACCCATGCTAAGTCCTG | 212 | ACGTTGGATGAAGATTATGGAGGCCAGGAG | 233 | TCCCACCTCCTCCGTGC | 254 |
| rs9940995 | ACGTTGGATGTCTGGAATGCCCCTTCTTAG | 213 | ACGTTGGATGGAGCATATTCTGAGGATGGG | 234 | GAACGTACCTCCCATGC | 255 |
| rs1122443 | ACGTTGGATGTTCCTTTTCTTCCAGATGGG | 214 | ACGTTGGATGGTATATAGCTGGGCATGGTG | 235 | GCCCAGGGTGAATTAAA | 256 |
| rs10761670 | ACGTTGGATGCTCTGTCACTGACTTCATGG | 215 | ACGTTGGATGTACTCAGAGGAACCTGAGTC | 236 | TGACTTCATGGGACCTCA | 257 |
| rs2560643 | ACGTTGGATGGGCTCTAAGCCATTCTTCTG | 216 | ACGTTGGATGGCCTTTCAAAGCCACATCTC | 237 | tTCCCCCTGTCCCTCTGCC | 258 |
| rs13134004 | ACGTTGGATGGGAGTTCTTATCCATACTATG | 217 | ACGTTGGATGGGAAGCTTCTGGGACTTAAT | 238 | TTTTCTGTGCTTTTTCCTC | 259 |
| rs11077442 | ACGTTGGATGAACTCCCATTTCTCCCTGTG | 218 | ACGTTGGATGTGGACCCAGTCAAGAAAGTC | 239 | gaTCCCTGTGTGGTAATGC | 260 |
| rs4924176 | ACGTTGGATGGGTTTCATTCCCAACAAGTC | 219 | ACGTTGGATGCAGCCTATGTATGGAACAG | 240 | AATGCCACATTCTTGATTGC | 261 |
| rs6005955 | ACGTTGGATGTTAAGCACTGCCTGTATCCC | 220 | ACGTTGGATGGGGCAGTGAACTTGTCTAC | 241 | ggaAGTGTGCTAGACGCTGC | 262 |
| rs9893096 | ACGTTGGATGAACCCACTATACCCCAACTC | 221 | ACGTTGGATGACACACACATTCTGCTGAGG | 242 | ccccAGGCCCAAGTCTTCTGC | 263 |
| rs7241823 | ACGTTGGATGTAACTTGATTACTGGCACTG | 222 | ACGTTGGATGCCAGGTGTGTCTCAAAATTC | 243 | ggggACTGGCACTGCCCCATA | 264 |
| rs6026436 | ACGTTGGATGCTCAAAGGTGCCAATCACTC | 223 | ACGTTGGATGCTGATGGCTTGTCTTGATTC | 244 | aCACAGGCCCATAAACTATAAC | 265 |
| rs7926887 | ACGTTGGATGCTGAACAAGACCTTGAAG | 224 | ACGTTGGATGGTTGAGACTGCCAGCTATTC | 245 | ggACAAGACCTTGAAGTTGATA | 266 |
| rs17811318 | ACGTTGGATGTACAACTGGATGCTGAGTAG | 225 | ACGTTGGATGTTAGACATGAGGCCCCAAAG | 246 | aAAAAGAGAGTTGAAGTTTAGG | 267 |
| rs578381 | ACGTTGGATGTGTTTCCTTGAGGCTCTCTG | 226 | ACGTTGGATGAACAGGTCTGACATGGTGG | 247 | gttgcGGCTCTCTGTTGTCTGTT | 268 |
| rs978055 | ACGTTGGATGTTCCAAGATCCCCCTTTTCC | 227 | ACGTTGGATGGGCATAAAGCCTTACACCTC | 248 | gaaccTTTACTTGCTTCCTGTTGC | 269 |
| rs17627583 | ACGTTGGATGTGGATCTTACCCCTATTCAG | 228 | ACGTTGGATGTTGGTGTGACCAAGACCTAC | 249 | gTCAGATAAAGTCTGAGTTCATTG | 270 |
| rs2887761 | ACGTTGGATGTCTGATGGTATGTAGAGAGG | 229 | ACGTTGGATGGGGCAAATTTCCATTTGTG | 250 | ATGGTATGTAGAGAGGTAAATTGC | 271 |

TABLE 11-continued

| SNP ID | Amplification primer | SEQ ID NO: | Amplification primer | SEQ ID NO: | Extend Primer sequence | SEQ ID NO: |
|---|---|---|---|---|---|---|
| rs7702915 | ACGTTGGATGTCCCATAGTCTGATCCCTAC | 230 | ACGTTGGATGGATGTTCTCCAAAGTAGAAG | 251 | ggagaATCCCTACCTGATGTTTTGC | 272 |
| rs4998490 | ACGTTGGATGCCAGGAATTGGGATATGGAC | 231 | ACGTTGGATGCCAAGCTTCAAATCAATGTG | 252 | tCTTACCACTAAAAAACTATCAGTAT | 273 |
| rs9306015 | ACGTTGGATGGCCTGGGAAAATGATTGGAC | 232 | ACGTTGGATGGTGGGAGATATTGTTAAGGC | 253 | AATATTTTGAGATAAATTGTAGATGC | 274 |

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, yet these modifications and improvements are within the scope and spirit of the invention.

The invention illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the invention claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" is about 1, about 2 and about 3). For example, a weight of "about 100 grams" can include weights between 90 grams and 110 grams. Thus, it should be understood that although the present invention has been specifically disclosed by representative embodiments and optional features, modification and variation of the concepts herein disclosed may be resorted to by those skilled in the art, and such modifications and variations are considered within the scope of this invention.

Embodiments of the invention are set forth in the claims that follow.

What is claimed is:

1. A method for detecting the presence or absence of a plurality of target alleles at a plurality of polymorphic loci in a sample, wherein the sample contains maternal nucleic acid and fetal nucleic acid, which comprises:
   a) cleaving nucleic acid comprising a plurality of non-target alleles at the plurality of polymorphic loci with a single cleavage agent that recognizes the non-target alleles at single-nucleotide polymorphic loci, wherein the cleavage agent is a non-thermostable restriction endonuclease;
   b) elevating the temperature to a temperature that inactivates the endonuclease;
   c) after (b), amplifying uncleaved nucleic acid but not cleaved nucleic acid; and
   d) analyzing the amplification products of step (c) to determine the presence or absence of a plurality of target alleles, wherein
      the target alleles are of paternal origin and the non-target alleles are of maternal origin.

2. The method of claim 1, wherein the sample is from a pregnant female or a female suspected of being pregnant.

3. The method of claim 1, wherein 60 or more polymorphic loci are assayed.

4. The method of claim 1, wherein 10 or more target alleles are detected.

5. The method of claim 1, wherein the non-thermostable restriction endonuclease is HpyCH4V.

6. The method of claim 1, wherein the target allele concentration is less than 4% of the non-target allele concentration prior to cleaving and amplifying the nucleic acid.

7. The method of claim 1, wherein the single nucleotide polymorphic loci are selected from the group consisting of the polymorphisms rs10430091, rs2050927, rs4329520, rs4657868, rs4658481, rs6693568, rs860954 and rs9431593.

8. The method of claim 1, wherein the relative amount of fetal nucleic acid is enriched to at least 20% in part (c).

9. The method of claim 8, wherein in part (d) the presence or absence of a plurality of target alleles is determined with a sensitivity of at least 95% and a specificity of about 100%.

* * * * *

UNITED STATES PATENT AND TRADEMARK OFFICE
CERTIFICATE OF CORRECTION

| | | |
|---|---|---|
| PATENT NO. | : 8,652,780 B2 | Page 1 of 1 |
| APPLICATION NO. | : 12/532824 | |
| DATED | : February 18, 2014 | |
| INVENTOR(S) | : Mathias Ehrich et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 672 days.

Signed and Sealed this
Eighth Day of March, 2016

Michelle K. Lee
*Director of the United States Patent and Trademark Office*

SEQUENCE LISTING

```
<160> NUMBER OF SEQ ID NOS: 307

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
acgttggatg                                                           10

<210> SEQ ID NO 2
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, c, t, g, unknown or other

<400> SEQUENCE: 2
gccnnnnngg c                                                         11
```

```
<210> SEQ ID NO 3
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, c, t, g, unknown or other

<400> SEQUENCE: 3
cgannnnnnt gc                                                            12

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
acgttggatg cacaagattc tgaaacttag                                         30

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
acgttggatg ttgggtgcag agtagtcatc                                         30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
acgttggatg atgtccacct cctgctccac                                         30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
acgttggatg ctagcgtacc caatggaatc                                         30

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
```

```
acgttggatg gtggtagaaa caaatgtcag c                                       31
```

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

```
acgttggatg ggcctgttca ttctcagaaa                                         30
```

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

```
acgttggatg tagcctttag tcttgatgcc                                         30
```

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

```
acgttggatg gcctcagtag tcacataagg                                         30
```

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

```
acgttggatg gctgtttaac tcagcatg                                           28
```

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13

```
acgttggatg ttctagcttg cttctcctcc                                         30
```

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14

```
acgttggatg gaaagttgtc gtggtagagg                                         30
```

```
<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
acgttggatg ctaaccagga aaagacaccc                                    30

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
acgttggatg ctgctaagca tgagagaaag                                    30

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
acgttggatg tgactaggaa atcacactgg                                    30

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
acgttggatg ccattcttgt atgttttgtc                                    30

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
acgttggatg ttgagatcag tgtcggttcc                                    30

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gtgtttaact cagcatgtgg gaa                                           23
```

<210> SEQ ID NO 21
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cctccatcat ccttagc                                                    17

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gcgtggttct agacttatgc                                                 20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
caagacaccc ccatacatta                                                 20

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
taagcatgag agaaagggaa ag                                              22

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
atgaaatcac actggacatt tt                                              22

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gttttgtctt tttctgtata ctcatg                                          26

```
<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tgttcctgac tctcaaaat                                              19

<210> SEQ ID NO 28
<211> LENGTH: 31
<212> TYPE: DNA
<213> ORGANISM: Homo sapiens

<400> SEQUENCE: 28
cacacagtta ggattyacct gagcttgtcc c                                31

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
acgttggatg atccctggtt ccttccttag                                  30

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
acgttggatg atcctagata gcccaaagcc                                  30

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
acgttggatg atgctgtaaa gagcctcaac                                  30

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
acgttggatg tcagagagtg acaagacctg                                  30

<210> SEQ ID NO 33
<211> LENGTH: 30
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 33
acgttggatg cagagagtcc cctgttattg                                         30

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
acgttggatg gctacatact atgtggtctc                                         30

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
acgttggatg ttctagcttg cttctcctcc                                         30

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
acgttggatg caacatcctg tacatcactc                                         30

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
acgttggatg acaggcatga gccatcttac                                         30

<210> SEQ ID NO 38
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
acgttggatg taggtcaagc caaggcctc                                          29

<210> SEQ ID NO 39
<211> LENGTH: 30
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 39
acgttggatg agcatctagg taggtctttg                                        30

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
acgttggatg tttcagcaac cactctgagc                                        30

<210> SEQ ID NO 41
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
acgttggatg gaaatttctg gattactggc                                        30

<210> SEQ ID NO 42
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
acgttggatg ttgagatcag tgtcggttcc                                        30

<210> SEQ ID NO 43
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
acgttggatg cttcatccac tatatccacc                                        30

<210> SEQ ID NO 44
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
acgttggatg gaaagttgtc gtggtagagg                                        30

<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 45
acgttggatg ctgttaagat gccaactccc                                     30

<210> SEQ ID NO 46
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
acgttggatg gagtagttct ttgcagtaag c                                   31

<210> SEQ ID NO 47
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
acgttggatg attcttcctg ggactcagac                                     30

<210> SEQ ID NO 48
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
acgttggatg agctggccat gtttatttga c                                   31

<210> SEQ ID NO 49
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
acgttggatg ggaatcagac ctgtaaacac                                     30

<210> SEQ ID NO 50
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
acgttggatg aaagctctgt gatgcgtctc                                     30

<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
acgttggatg gagcctctca gtgtctatac          30

<210> SEQ ID NO 52
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
acgttggatg ggaggaaaga gaagattgtg          30

<210> SEQ ID NO 53
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
acgttggatg ttctcctctg acctgctttc          30

<210> SEQ ID NO 54
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
acgttggatg gaatgcatgc caacttaggg          30

<210> SEQ ID NO 55
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
acgttggatg tgcccagacc agagaggtca          30

<210> SEQ ID NO 56
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
acgttggatg cctgctggca acaaatcttc          30

<210> SEQ ID NO 57
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
acgttggatg ttgggtgcag agtagtcatc          30

<210> SEQ ID NO 58
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 58
acgttggatg agacaatttc tgtcctctgg                                    30

<210> SEQ ID NO 59
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 59
acgttggatg tgccattggt acagtcactc                                    30

<210> SEQ ID NO 60
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 60
acgttggatg tgtccaccca ggagcagcca                                    30

<210> SEQ ID NO 61
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 61
acgttggatg agcaacggga ccgctacag                                     29

<210> SEQ ID NO 62
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 62
acgttggatg tgcccgtaag taggagagtg                                    30

<210> SEQ ID NO 63
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 63
acgttggatg agagactcca tttgtttggg                                    30

<210> SEQ ID NO 64
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 64
acgttggatg gcctcagtag tcacataagg               30

<210> SEQ ID NO 65
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 65
acgttggatg tgaccagatg ttggattag                29

<210> SEQ ID NO 66
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 66
acgttggatg atgtccacct cctgctccac               30

<210> SEQ ID NO 67
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 67
acgttggatg ctgtcttcct cattgctctg               30

<210> SEQ ID NO 68
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 68
acgttggatg ctcctggaaa acagcaaaag               30

<210> SEQ ID NO 69
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 69
acgttggatg ggaaatacca gcaaccacag               30

<210> SEQ ID NO 70
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
acgttggatg gccaatctat gaagaattac                               30

<210> SEQ ID NO 71
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
acgttggatg gcccagcagg acacttttat                               30

<210> SEQ ID NO 72
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
acgttggatg gaaagggcta tgtaaggagg                               30

<210> SEQ ID NO 73
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
ggacagattc tgggac                                              16

<210> SEQ ID NO 74
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
ccaaagccaa gaattca                                             17

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
cctcaacagt acacttaatc                                          20

```
<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
caggtcacac agttaggatt                                                    20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
atggaccttc ggaaaggata                                                    20

<210> SEQ ID NO 78
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
tactatgtgg tctcaactat at                                                 22

<210> SEQ ID NO 79
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
tgcttctcct ccatcatcct tagc                                               24

<210> SEQ ID NO 80
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
tacatgacta tctcctccct taggt                                              25

<210> SEQ ID NO 81
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ccatcttacc cagcctcttt cttcaa                                             26
```

<210> SEQ ID NO 82
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
ggccaaggcc tcggagtctg aacagtt                                         27

<210> SEQ ID NO 83
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
cgttacccga ttgtcctac                                                  19

<210> SEQ ID NO 84
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
cttgatgtgc ttccctg                                                    17

<210> SEQ ID NO 85
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
tggattactg gcaaagac                                                   18

<210> SEQ ID NO 86
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
tgttcctgac tctcaaaat                                                  19

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
ccactatatc cacctttct                                                  20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
gcgtggttct agacttatgc                                               20

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
aactcccata ttagtccaca g                                             21

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
ggcagtaagc tattcttggg g                                             21

<210> SEQ ID NO 91
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
catcgggatt ccctgaacaa aa                                            22

<210> SEQ ID NO 92
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
atttgacttt cctactcctt aac                                           23

<210> SEQ ID NO 93
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
ccttcaagga ttggaattag agt                                           23

<210> SEQ ID NO 94
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
tcgtctcggt ccttccttt cactt                                           25

<210> SEQ ID NO 95
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
acgttggatg aagagatgag acagactggg                                     30

<210> SEQ ID NO 96
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
acgttggatg atctctgagt tgacaccacc                                     30

<210> SEQ ID NO 97
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
acgttggatg tttcagcaac cactctgagc                                     30

<210> SEQ ID NO 98
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
acgttggatg gaaatttctg gattactggc                                     30

<210> SEQ ID NO 99
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
acgttggatg ttgagatcag tgtcggttcc                                     30

<210> SEQ ID NO 100
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 100
acgttggatg cttcatccac tatatccacc          30

<210> SEQ ID NO 101
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 101
acgttggatg gaaagttgtc gtggtagagg          30

<210> SEQ ID NO 102
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 102
acgttggatg ctgttaagat gccaactccc          30

<210> SEQ ID NO 103
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 103
acgttggatg gagtagttct ttgcagtaag c          31

<210> SEQ ID NO 104
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 104
acgttggatg attcttcctg ggactcagac          30

<210> SEQ ID NO 105
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 105
acgttggatg agctggccat gtttatttga c          31

<210> SEQ ID NO 106
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 106
acgttggatg ggaatcagac ctgtaaacac        30

<210> SEQ ID NO 107
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 107
acgttggatg gcttgtgctt tgttgtgtgg        30

<210> SEQ ID NO 108
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 108
acgttggatg aaagctctgt gatgcgtctc        30

<210> SEQ ID NO 109
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 109
acgttggatg acccgagcca atcaggtatc        30

<210> SEQ ID NO 110
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 110
acgttggatg tgcgtcaacc tttccagttc        30

<210> SEQ ID NO 111
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 111
acgttggatg ccagtcaagc taaggacaaa        30

<210> SEQ ID NO 112
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 112
acgttggatg ggactaaaac agggccaaac                30

<210> SEQ ID NO 113
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 113
acgttggatg tcttctaaaa tgtagttatg                30

<210> SEQ ID NO 114
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 114
acgttggatg ccaaaaaacc atgccctctg                30

<210> SEQ ID NO 115
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 115
acgttggatg ctgccgcatc ccttcacaa                 29

<210> SEQ ID NO 116
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 116
acgttggatg aaaggcctac tgtttgctgg                30

<210> SEQ ID NO 117
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 117
acgttggatg gctcaactct gaaccaatcg                30

```
<210> SEQ ID NO 118
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
acgttggatg ctaaccagga aaagacaccc                                    30

<210> SEQ ID NO 119
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
acgttggatg taaatcaggg ctgccttctc                                    30

<210> SEQ ID NO 120
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
acgttggatg tgtgcaaatt ggctaacat                                     29

<210> SEQ ID NO 121
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
acgttggatg agacaatttc tgtcctctgg                                    30

<210> SEQ ID NO 122
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
acgttggatg atcaagagga aaatggacag                                    30

<210> SEQ ID NO 123
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
acgttggatg gtgcatgggc tcatctagac                                    30
```

<210> SEQ ID NO 124
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 124
acgttggatg ctattccctc ctcaaagagc                               30

<210> SEQ ID NO 125
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 125
acgttggatg tatgttactt gccttggccc                               30

<210> SEQ ID NO 126
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 126
acgttggatg ggttctatgg ctttggtgag                               30

<210> SEQ ID NO 127
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 127
acgttggatg ctgctaagca tgagagaaag                               30

<210> SEQ ID NO 128
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 128
acgttggatg ccaaatgtct tagttacaaa g                             31

<210> SEQ ID NO 129
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 129
acgttggatg tagcctttag tcttgatgcc                               30

<210> SEQ ID NO 130
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
acgttggatg gaggagctaa caagtaggac                                    30

<210> SEQ ID NO 131
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
acgttggatg gagattatat gtctctttaa                                    30

<210> SEQ ID NO 132
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
acgttggatg ctaatgcctc cttttcttcc                                    30

<210> SEQ ID NO 133
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
acgttggatg gaatcctggc agctcattag                                    30

<210> SEQ ID NO 134
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
acgttggatg ctctgtattt atagctttc                                     29

<210> SEQ ID NO 135
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
acgttggatg ttcctaatca ggagagaccg                                    30

<210> SEQ ID NO 136
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
acgttggatg tgcccgtaag taggagagtg                                    30

<210> SEQ ID NO 137
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
acgttggatg agagactcca tttgtttggg                                    30

<210> SEQ ID NO 138
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
acgttggatg gcctcagtag tcacataagg                                    30

<210> SEQ ID NO 139
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
acgttggatg tgaccagatg ttggattag                                     29

<210> SEQ ID NO 140
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
acgttggatg atgtccacct cctgctccac                                    30

<210> SEQ ID NO 141
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
acgttggatg ctgtcttcct cattgctctg                                    30

<210> SEQ ID NO 142
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 142
acgttggatg ctcctggaaa acagcaaaag     30

<210> SEQ ID NO 143
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 143
acgttggatg ggaaatacca gcaaccacag     30

<210> SEQ ID NO 144
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 144
acgttggatg gccaatctat gaagaattac     30

<210> SEQ ID NO 145
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 145
acgttggatg gcccagcagg acacttttat     30

<210> SEQ ID NO 146
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 146
acgttggatg ggtcaagcaa aggcttcaag     30

<210> SEQ ID NO 147
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 147
acgttggatg gaaagggcta tgtaaggagg     30

```
<210> SEQ ID NO 148
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
acgttggatg gcacatggag atgaatggtc                                         30

<210> SEQ ID NO 149
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
acgttggatg ggaaagtcct cgactgtttg                                         30

<210> SEQ ID NO 150
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
acgttggatg gtgagcacaa ctgtgttcta                                         30

<210> SEQ ID NO 151
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
acgttggatg gtctctctag tactagtaac                                         30

<210> SEQ ID NO 152
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
acgttggatg ggatgaggtt ttgactaagc                                         30

<210> SEQ ID NO 153
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
acgttggatg agattgcctc tccatgtgac                                         30
```

<210> SEQ ID NO 154
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 154
acgttggatg atgtgtttgt ggccacttcc                               30

<210> SEQ ID NO 155
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 155
acgttggatg caaaatatgt gtgaatcagc                               30

<210> SEQ ID NO 156
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 156
acgttggatg ccaggaatgg gcatgtgttc                               30

<210> SEQ ID NO 157
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 157
acgttggatg ctagcgtacc caatggaatc                               30

<210> SEQ ID NO 158
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 158
acgttggatg aagtgctagg gttacaggtg                               30

<210> SEQ ID NO 159
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 159
acgttggatg gaacattggt atttaaactc                               30

<210> SEQ ID NO 160
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
acgttggatg caacatcctg tacatcactc                                      30

<210> SEQ ID NO 161
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
acgttggatg gatttactca actctctggg                                      30

<210> SEQ ID NO 162
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
acgttggatg ccaaacaggg ccaatggtag                                      30

<210> SEQ ID NO 163
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
acgttggatg attaagatgg gtagttaag                                       29

<210> SEQ ID NO 164
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
acgttggatg tcttaaggtg tctccctctg                                      30

<210> SEQ ID NO 165
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
acgttggatg tgctagacac tttaactgcc                                      30

<210> SEQ ID NO 166
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
acgttggatg gtggtagaaa caaatgtcag c         31

<210> SEQ ID NO 167
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
acgttggatg gagtttatgt aatgtcaac           29

<210> SEQ ID NO 168
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
acgttggatg ccattcttgt atgttttgtc          30

<210> SEQ ID NO 169
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
acgttggatg gggatatgaa ttacaacaga g         31

<210> SEQ ID NO 170
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
acgttggatg attcttctaa cttttaggc           29

<210> SEQ ID NO 171
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
acgttggatg aatagcaaac aacaggtggg          30

```
<210> SEQ ID NO 172
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
acgttggatg tgggttcaca tgagtcttgc                                           30

<210> SEQ ID NO 173
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
aacggctcaa cagtt                                                           15

<210> SEQ ID NO 174
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
ttgctttggg gagcag                                                          16

<210> SEQ ID NO 175
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
cttgatgtgc ttccctg                                                         17

<210> SEQ ID NO 176
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
tggattactg gcaaagac                                                        18

<210> SEQ ID NO 177
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
tgttcctgac tctcaaaat                                                       19
```

<210> SEQ ID NO 178
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
ccactatatc cacctttct                                                  20

<210> SEQ ID NO 179
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
gcgtggttct agacttatgc                                                 20

<210> SEQ ID NO 180
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
aactcccata ttagtccaca g                                               21

<210> SEQ ID NO 181
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
ggcagtaagc tattcttggg g                                               21

<210> SEQ ID NO 182
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
catcgggatt ccctgaacaa aa                                              22

<210> SEQ ID NO 183
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
atttgacttt cctactcctt aac                                             23

<210> SEQ ID NO 184
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
ccttcaagga ttggaattag agt                                              23

<210> SEQ ID NO 185
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
acatagttat tcctagggct tctc                                             24

<210> SEQ ID NO 186
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
tcgtctcggt ccttcctttt cactt                                            25

<210> SEQ ID NO 187
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
ggtatcataa datacctatg atgtc                                            25

<210> SEQ ID NO 188
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
ggaatttcca gttctattcc agcctc                                           26

<210> SEQ ID NO 189
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
tccctgaatg acaaaagggg aagata                                           26

```
<210> SEQ ID NO 190
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
ccctcgccaa acttagacca aggacaac                                            28

<210> SEQ ID NO 191
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
agttatgaaa taagttttat tcatttac                                            28

<210> SEQ ID NO 192
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
cctctgcctc cccta                                                          15

<210> SEQ ID NO 193
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
ccttcacaaa gccga                                                          15

<210> SEQ ID NO 194
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
cgtttgctgg aagcct                                                         16

<210> SEQ ID NO 195
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
tggccagaag aaggag                                                         16
```

-continued

```
<210> SEQ ID NO 196
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
agacaccccc atacatta                                                        18

<210> SEQ ID NO 197
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
cccctgcctt ctcttccaa                                                       19

<210> SEQ ID NO 198
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
atggaccaca aaaaactta                                                       19

<210> SEQ ID NO 199
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
tctgtcctct ggtatcctct                                                      20

<210> SEQ ID NO 200
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
caaaatggac agaagttgaa                                                      20

<210> SEQ ID NO 201
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
gcatctagac acattttgtg c                                                    21
```

<210> SEQ ID NO 202
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
tccaagagca tttttcctct tc                                              22

<210> SEQ ID NO 203
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
ggaccactga ggagatacac ta                                              22

<210> SEQ ID NO 204
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
ggtcacctct tttcataaca gga                                             23

<210> SEQ ID NO 205
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
atacgcatga gagaaaggga aag                                             23

<210> SEQ ID NO 206
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
cttagttaca aagaaaattg tgag                                            24

<210> SEQ ID NO 207
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
tcttgatgcc ttacaaaata aatat                                           25

```
<210> SEQ ID NO 208
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
aaacaaatcc tcctttcttt taattc                                           26

<210> SEQ ID NO 209
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
gagattatat gtctctttaa tattgtc                                          27

<210> SEQ ID NO 210
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
cccccatatc atttgcaatt gcatggtt                                         28

<210> SEQ ID NO 211
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
gatgtctctt aaagagcaaa aagctaag                                         28

<210> SEQ ID NO 212
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
acgttggatg cttacccatg ctaagtcctg                                       30

<210> SEQ ID NO 213
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
acgttggatg tctggaatgc cccttcttag                                       30
```

<210> SEQ ID NO 214
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
acgttggatg ttccttttct tccagatggg                                    30

<210> SEQ ID NO 215
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215
acgttggatg ctctgtcact gacttcatgg                                    30

<210> SEQ ID NO 216
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
acgttggatg ggctctaagc cattcttctg                                    30

<210> SEQ ID NO 217
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
acgttggatg ggagttctta tccatactat g                                  31

<210> SEQ ID NO 218
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
acgttggatg aactcccatt tctccctgtg                                    30

<210> SEQ ID NO 219
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
acgttggatg ggtttcattc ccaacaagtc                                    30

<210> SEQ ID NO 220
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
acgttggatg ttaagcactg cctgtatccc                                    30

<210> SEQ ID NO 221
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
acgttggatg aacccactat accccaactc                                    30

<210> SEQ ID NO 222
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222
acgttggatg taacttgatt actggcactg                                    30

<210> SEQ ID NO 223
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
acgttggatg ctcaaaggtg ccaatcactc                                    30

<210> SEQ ID NO 224
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224
acgttggatg ctgaacaaga ccttgaag                                      28

<210> SEQ ID NO 225
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
acgttggatg tacaactgga tgctgagtag                                    30

<210> SEQ ID NO 226
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
acgttggatg tgtttccttg aggctctctg                                       30

<210> SEQ ID NO 227
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
acgttggatg ttccaagatc cccctttcc                                        30

<210> SEQ ID NO 228
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 228
acgttggatg tggatcttac ccctattcag                                       30

<210> SEQ ID NO 229
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
acgttggatg tctgatggta tgtagagagg                                       30

<210> SEQ ID NO 230
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
acgttggatg tcccatagtc tgatccctac                                       30

<210> SEQ ID NO 231
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 231
acgttggatg ccaggaattg ggatatggac                                    30

<210> SEQ ID NO 232
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
acgttggatg gcctgggaaa atgattggac                                    30

<210> SEQ ID NO 233
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
acgttggatg aagattatgg aggccaggag                                    30

<210> SEQ ID NO 234
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 234
acgttggatg gagcatattc tgaggatggg                                    30

<210> SEQ ID NO 235
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
acgttggatg gtatatagct gggcatggtg                                    30

<210> SEQ ID NO 236
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 236
acgttggatg tactcagagg aacctgagtc                                    30

<210> SEQ ID NO 237
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237
```
acgttggatg gcctttcaaa gccacatctc                                30

<210> SEQ ID NO 238
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238
acgttggatg ggaagcttct gggacttaat                                30

<210> SEQ ID NO 239
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239
acgttggatg tggacccagt caagaaagtc                                30

<210> SEQ ID NO 240
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 240
acgttggatg cagcctatgt atggaaacag                                30

<210> SEQ ID NO 241
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 241
acgttggatg gggcagtgaa cttgtctac                                 29

<210> SEQ ID NO 242
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 242
acgttggatg acacacacat tctgctgagg                                30

<210> SEQ ID NO 243
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 243
acgttggatg ccaggtgtgt ctcaaaattc                                30

<210> SEQ ID NO 244
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 244
acgttggatg ctgatggctt gtcttgattc                           30

<210> SEQ ID NO 245
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 245
acgttggatg gttgagactg ccagctattc                           30

<210> SEQ ID NO 246
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 246
acgttggatg ttagacatga ggccccaaag                           30

<210> SEQ ID NO 247
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 247
acgttggatg aacaggtctg acatctgtgg                           30

<210> SEQ ID NO 248
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 248
acgttggatg ggcataaagc cttacacctc                           30

<210> SEQ ID NO 249
<211> LENGTH: 30
<212> TYPE: DNA
<213> ORGANISM: Artificial Sequence
<220> FEATURE:
<223> OTHER INFORMATION: Description of Artificial Sequence: Synthetic primer

```
<400> SEQUENCE: 249
acgttggatg ttggtgtgac caagacctac                                       30

<210> SEQ ID NO 250
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 250
acgttggatg gggcaaattt ccatttgtg                                        29

<210> SEQ ID NO 251
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 251
acgttggatg gatgttctcc aaagtagaag                                       30

<210> SEQ ID NO 252
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 252
acgttggatg ccaagcttca aatcaatgtg                                       30

<210> SEQ ID NO 253
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 253
acgttggatg gtgggagata ttgttaaggc                                       30

<210> SEQ ID NO 254
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 254
tcccacctcc tccgtgc                                                     17

<210> SEQ ID NO 255
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 255
```

-continued

```
gaacgtacct cccatgc                                            17

<210> SEQ ID NO 256
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 256
gcccagggtg aattaaa                                            17

<210> SEQ ID NO 257
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 257
tgacttcatg ggacctca                                           18

<210> SEQ ID NO 258
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 258
ttccccctgt ccctctgcc                                          19

<210> SEQ ID NO 259
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 259
ttttctgtgc tttttcctc                                          19

<210> SEQ ID NO 260
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 260
gatccctgtg tggtaatgc                                          19

<210> SEQ ID NO 261
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 261
aatgccacat tcttgattgc                                         20
```

<210> SEQ ID NO 262
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 262
ggaagtgtgc tagacgctgc                                               20

<210> SEQ ID NO 263
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 263
ccccaggccc aagtcttctg c                                             21

<210> SEQ ID NO 264
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 264
ggggactggc actgccccat a                                             21

<210> SEQ ID NO 265
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 265
acacaggccc ataaactata ac                                            22

<210> SEQ ID NO 266
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 266
ggacaagacc ttgaagttga ta                                            22

<210> SEQ ID NO 267
<211> LENGTH: 22
<212> TYPE: DNA
<213> ORGANISM: Artificial Sequence
<220> FEATURE:
<223> OTHER INFORMATION: Description of Artificial Sequence: Synthetic primer

```
<400> SEQUENCE: 267
aaaaagagag ttgaagttta gg                                              22

<210> SEQ ID NO 268
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 268
gttgcggctc tctgttgtct gtt                                             23

<210> SEQ ID NO 269
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 269
gaacctttac ttgcttcctg ttgc                                            24

<210> SEQ ID NO 270
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 270
gtcagataaa gtctgagttc attg                                            24

<210> SEQ ID NO 271
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 271
atggtatgta gagaggtaaa ttgc                                            24

<210> SEQ ID NO 272
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 272
ggagaatccc tacctgatgt tttgc                                           25

<210> SEQ ID NO 273
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 273
```

```
tcttaccact aaaaaactat cagtat                                            26

<210> SEQ ID NO 274
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 274
aatattttga gataaattgt agatgc                                            26

<210> SEQ ID NO 275
<211> LENGTH: 212
<212> TYPE: DNA
<213> ORGANISM: Homo sapiens

<400> SEQUENCE: 275
acctcatcct gggcaccctg gttatatcaa cttcagctat gaggtaattt ttctctttac       60 taatttttgac cattgtttgc gttaacaatg ccctgggctc tgtaaagaat agtgtgttga     120
ttctttatcc cagatgtttc tcaagtggtc ctgattttac agttcctacc accagcttcc     180
cagtttaagc tctgatggtt ggcctcaagc ct                                    212

<210> SEQ ID NO 276
<211> LENGTH: 218
<212> TYPE: DNA
<213> ORGANISM: Homo sapiens

<400> SEQUENCE: 276
acctcatcct gggcaccctg gttatatcaa cttcagctat gaggtaattt ttctctttac       60 taatttttgat cactgtttgc attagcagtc ccctgggctc tgtaaagaat agtgggtgga    120
ttcttcatcc caaataaagt ggtttctcaa gtggtcccaa ttttacagtt cctaccatca     180
gcttcccagt ttaagctctg atggttggcc tcaagcct                              218

<210> SEQ ID NO 277
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 277
acgttggatg ccctgggctc tgtaaagaat                                        30

<210> SEQ ID NO 278
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 278
acgttggatg aggcttgagg ccaaccatca g                                      31

<210> SEQ ID NO 279
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 279
ttcttcatcc caaataaagt                                                    20

<210> SEQ ID NO 280
<211> LENGTH: 122
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 280
ccctgggctc tgtaaagaat agtgtgttga ttctttatcc cagaagtttc tcaagtggtc        60
ctgattttac agttcctacc accagcttcc cagtttaagc tctgatggtt ggcctcaagc      120
ct                                                                      122

<210> SEQ ID NO 281
<211> LENGTH: 122
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 281
aggcttgagg ccaaccatca gagcttaaac tgggaagctg gtggtaggaa ctgtaaaatc        60
aggaccactt gagaaacttc tgggataaag aatcaacaca ctattcttta cagagcccag      120
gg                                                                      122

<210> SEQ ID NO 282
<211> LENGTH: 128
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 282
ccctgggctc tgtaaagaat agtgggtgga ttcttcatcc caaataaagt cgtttctcaa        60
gtggtcccaa ttttacagtt cctaccatca gcttcccagt ttaagctctg atggttggcc      120
tcaagcct                                                                128

<210> SEQ ID NO 283
<211> LENGTH: 128
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 283
aggcttgagg ccaaccatca gagcttaaac tgggaagctg atggtaggaa ctgtaaaatt        60
gggaccactt gagaaacgac tttatttggg atgaagaatc cacccactat tctttacaga      120
gcccaggg                                                                128

<210> SEQ ID NO 284
<211> LENGTH: 212
<212> TYPE: DNA
<213> ORGANISM: Homo sapiens
```

```
<400> SEQUENCE: 284
acctcatcct gggcaccctg gttatatcaa cttcagctat gaggtaattt ttctctttac      60
taattttgac cattgtttgc gttaacaatg ccctgggctc tgtaaagaat agtgtgttga     120
ttctttatcc cagatgtttc tcaagtggtc ctgattttac agttcctacc accagcttcc    180
cagtttaagc tctgatggtt ggcctcaagc ct                                  212

<210> SEQ ID NO 285
<211> LENGTH: 218
<212> TYPE: DNA
<213> ORGANISM: Homo sapiens

<400> SEQUENCE: 285
acctcatcct gggcaccctg gttatatcaa cttcagctat gaggtaattt ttctctttac      60
taattttgat cactgtttgc attagcagtc ccctgggctc tgtaaagaat agtgggtgga    120
ttcttcatcc caaataaagt ggtttctcaa gtggtcccaa ttttacagtt cctaccatca    180
gcttcccagt ttaagctctg atggttggcc tcaagcct                            218

<210> SEQ ID NO 286
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 286
acgttggatg tatcaacttc agctatgagg                                      30

<210> SEQ ID NO 287
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 287
acgttggatg cactattctt tacagagc                                        28

<210> SEQ ID NO 288
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 288
ctttacagag cccaggg                                                    17

<210> SEQ ID NO 289
<211> LENGTH: 90
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 289
tatcaacttc agctatgagg taattttct ctttactaat tttgaycayt gtttgcrtta      60
rcartaccct gggctctgta aagaatagtg                                      90
```

<210> SEQ ID NO 290
<211> LENGTH: 90
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 290
cactattctt tacagagccc agggtartgr taargcaaac aytgytcaaa attagtaaag      60
agaaaaatta cctcatagct gaagttgata                                      90

<210> SEQ ID NO 291
<211> LENGTH: 212
<212> TYPE: DNA
<213> ORGANISM: Homo sapiens

<400> SEQUENCE: 291
acctcatcct gggcaccctg gttatatcaa cttcagctat gaggtaattt ttctctttac      60
taattttgac cattgtttgc gttaacaatg ccctgggctc tgtaaagaat agtgtgttga     120
ttctttatcc cagatgtttc tcaagtggtc ctgattttac agttcctacc accagcttcc    180
cagtttaagc tctgatggtt ggcctcaagc ct                                  212

<210> SEQ ID NO 292
<211> LENGTH: 218
<212> TYPE: DNA
<213> ORGANISM: Homo sapiens

<400> SEQUENCE: 292
acctcatcct gggcaccctg gttatatcaa cttcagctat gaggtaattt ttctctttac      60
taattttgat cactgtttgc attagcagtc ccctgggctc tgtaaagaat agtgggtgga    120
ttcttcatcc caaataaagt ggtttctcaa gtggtcccaa ttttacagtt cctaccatca    180
gcttcccagt ttaagctctg atggttggcc tcaagcct                            218

<210> SEQ ID NO 293
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 293
ccctgggctc tgtaaagaat                                                 20

<210> SEQ ID NO 294
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 294
gagcttaaac tgggaagctg                                                 20

<210> SEQ ID NO 295
<211> LENGTH: 23
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 295
ccctgggctc tgtaaagaat agt                                            23

<210> SEQ ID NO 296
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 296
ttcttcatcc caaataaagt g                                              21

<210> SEQ ID NO 297
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 297
ccctgggctc tgtaaagaat agtg                                           24

<210> SEQ ID NO 298
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 298
ctgggctctg taaagaatag t                                              21

<210> SEQ ID NO 299
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 299
ctgggctctg taaagaatag tg                                             22

<210> SEQ ID NO 300
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 300
caggacagca gtagagca                                                  18

<210> SEQ ID NO 301
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 301
caggacagca gtagagcag        19

<210> SEQ ID NO 302
<211> LENGTH: 68
<212> TYPE: DNA
<213> ORGANISM: Homo sapiens

<400> SEQUENCE: 302
gctcagtatc ttcagcagtg tccatttgaa gatcatgtaa aattagtgaa tgaagtaact    60
gaatttgc    68

<210> SEQ ID NO 303
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 303
acgttggatg cagtatcttc agcagtgtcc    30

<210> SEQ ID NO 304
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 304
acgttggatg gcaaattcag ttacttcatt c    31

<210> SEQ ID NO 305
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 305
cagtgtccat ttgaagatc    19

<210> SEQ ID NO 306
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 306
cagtatcttc agcagtgtcc atttgaagat cttgtaaaat tagtgaatga agtaactgaa    60
tttgc    65

<210> SEQ ID NO 307
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 307
gcaaattcag ttacttcatt cactaatttt acaagatctt caaatggaca ctgctgaaga      60
tactg                                                                  65
```